United States Patent
Bacich et al.

[11] Patent Number: 5,772,628
[45] Date of Patent: Jun. 30, 1998

[54] SURGICAL ACCESS DEVICE AND METHOD OF CONSTRUCTING SAME

[75] Inventors: Steven R. Bacich, Laguna Niguel; John P. Greelis, Aliso Viejo; Hien Nguyen, Santa Ana; Tuoc Nguyen, Westminster, all of Calif.

[73] Assignee: Imagyn Medical, Inc., Laguna Niguel, Calif.

[21] Appl. No.: 600,603

[22] Filed: Feb. 13, 1996

[51] Int. Cl.⁶ .................................................. A61M 25/00
[52] U.S. Cl. ............................................. 604/43; 604/280
[58] Field of Search ............................. 606/198; 604/43, 604/265, 280, 178, 52, 53, 264; 128/2

[56] References Cited

U.S. PATENT DOCUMENTS

| | | |
|---|---|---|
| 2,548,602 | 4/1951 | Greenburg . |
| 3,789,852 | 2/1974 | Kim . |
| 4,141,364 | 2/1979 | Schultze . |
| 4,211,234 | 7/1980 | Fisher . |
| 4,350,147 | 9/1982 | Sarrine . |
| 4,406,656 | 9/1983 | Hattler et al. . |
| 4,601,713 | 7/1986 | Fuqua . |
| 4,646,722 | 3/1987 | Silverstein et al. . |
| 4,721,097 | 1/1988 | D'Amelio . |
| 4,738,666 | 4/1988 | Fuqua . |
| 4,798,193 | 1/1989 | Giesy et al. . |
| 4,800,870 | 1/1989 | Reid, Jr. . |
| 4,928,669 | 5/1990 | Sullivan . |
| 5,025,778 | 6/1991 | Silverstein et al. ................ 128/4 |
| 5,106,368 | 4/1992 | Uldall et al. .................... 604/280 |
| 5,201,908 | 4/1993 | Jones . |
| 5,213,092 | 5/1993 | Uram . |
| 5,217,001 | 6/1993 | Nakao et al. . |
| 5,232,446 | 8/1993 | Arney . |
| 5,318,588 | 6/1994 | Horzewski et al. . |
| 5,334,167 | 8/1994 | Cocanower ....................... 604/280 |
| 5,378,230 | 1/1995 | Mahurkar ........................... 604/43 |
| 5,386,817 | 2/1995 | Jones . |
| 5,413,560 | 5/1995 | Solar . |
| 5,503,616 | 4/1996 | Jones . |
| 5,573,508 | 11/1996 | Thornton . |

*Primary Examiner*—Michael Buiz
*Assistant Examiner*—Kevin Truong
*Attorney, Agent, or Firm*—Knobbe, Martens, Olson & Bear, LLP

[57] ABSTRACT

A surgical access device comprises an introducer with a main endoscopic channel and an auxiliary or secondary instrument channel. The introducer exhibits an extremely narrow cross-sectional profile in order to minimize the size of the portal or other entry point necessary to gain access into the patient's body, thereby minimizing pain and discomfort to the patient and allowing a wide variety of endoscopic procedures to be performed on an out-patient basis. The narrow profile of the introducer is maintained upon introduction by a guide channel which can be stored in a first position so as to closely conform to the profile of the introducer. The guide channel is provided with a set in order to maintain its stored position upon introduction; however, post introductively, the set in the guide channel can be readily released in order to deploy the guide channel and allow insertion of a secondary surgical instrument. The guide channel can be provided with rails or other tracks in order to ensure accurate movement of the instrument to the desired distal location. The guide channel is constructed from a thin but extremely strong and noncompliant membrane material. The present invention also comprises a method of construction and use of the surgical access device.

29 Claims, 14 Drawing Sheets

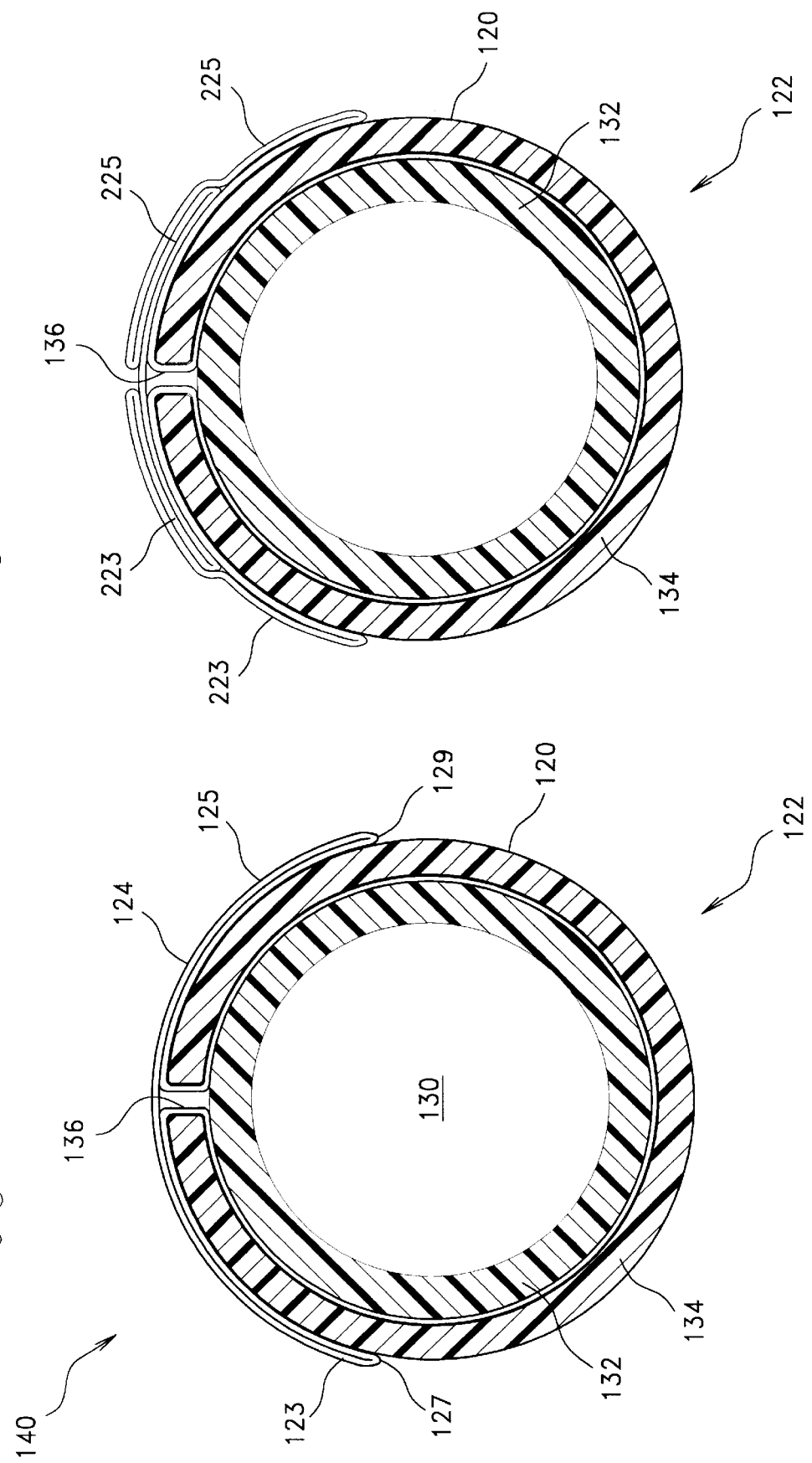

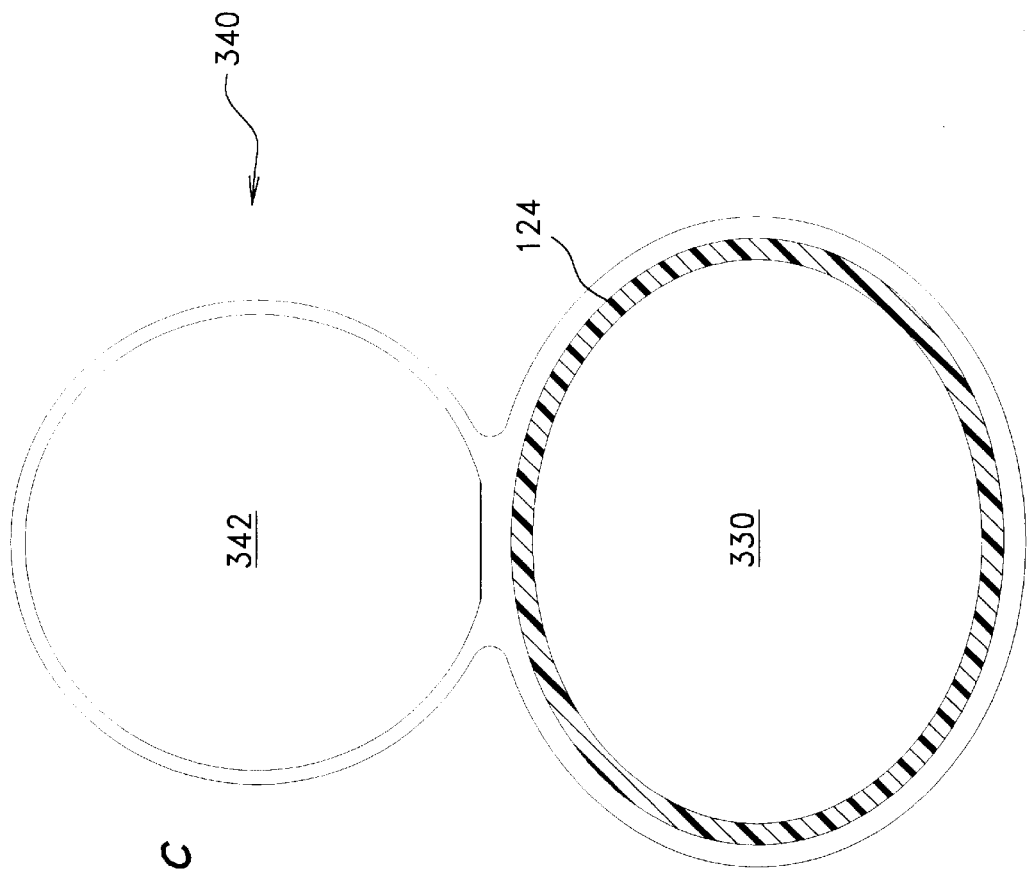
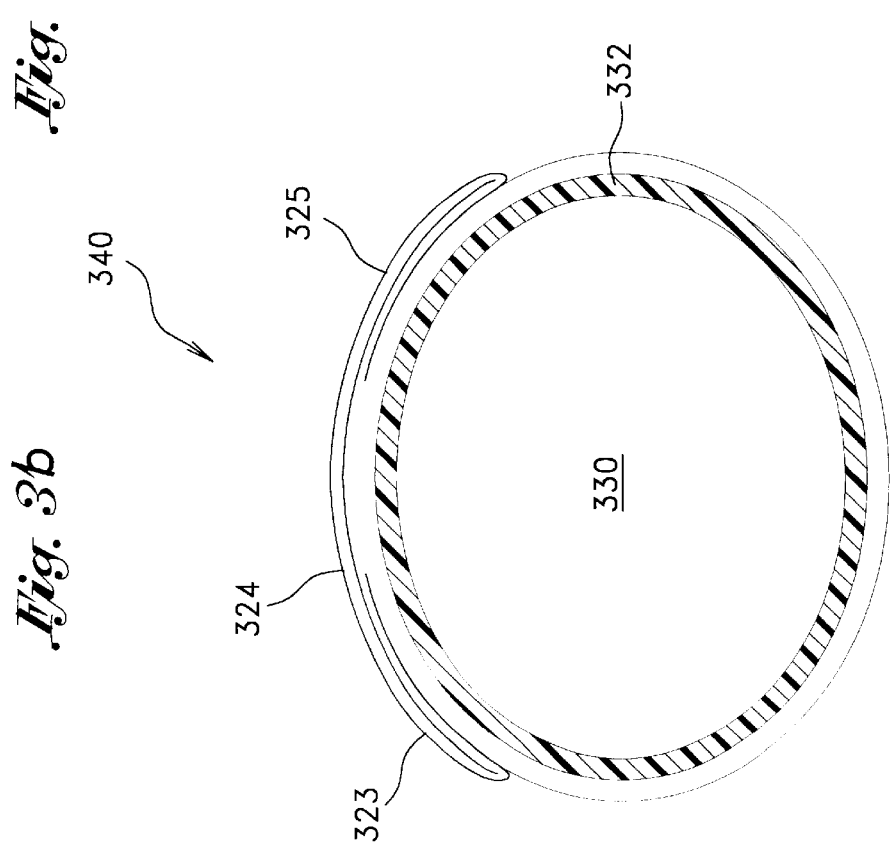
Fig. 3b
Fig. 3c

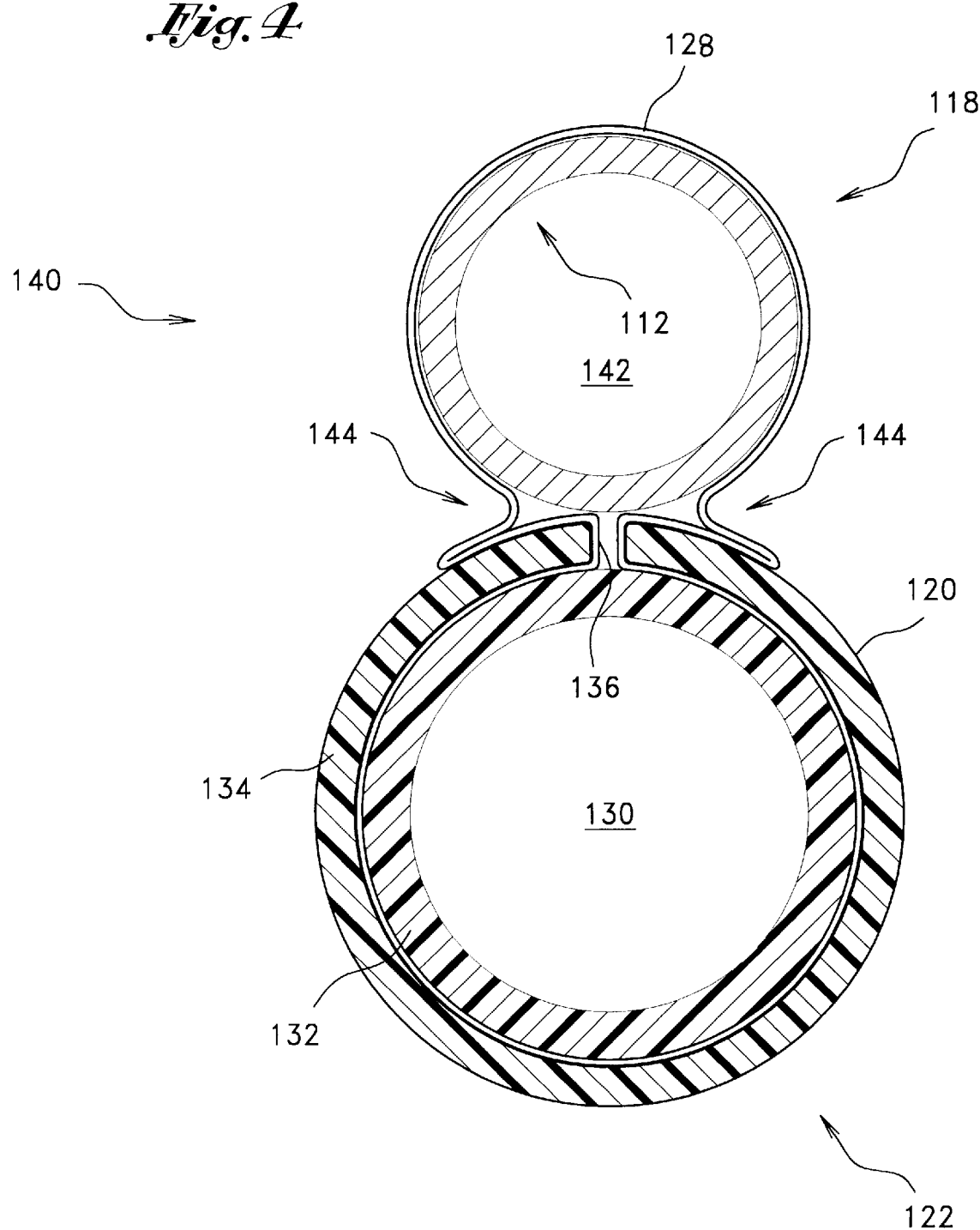

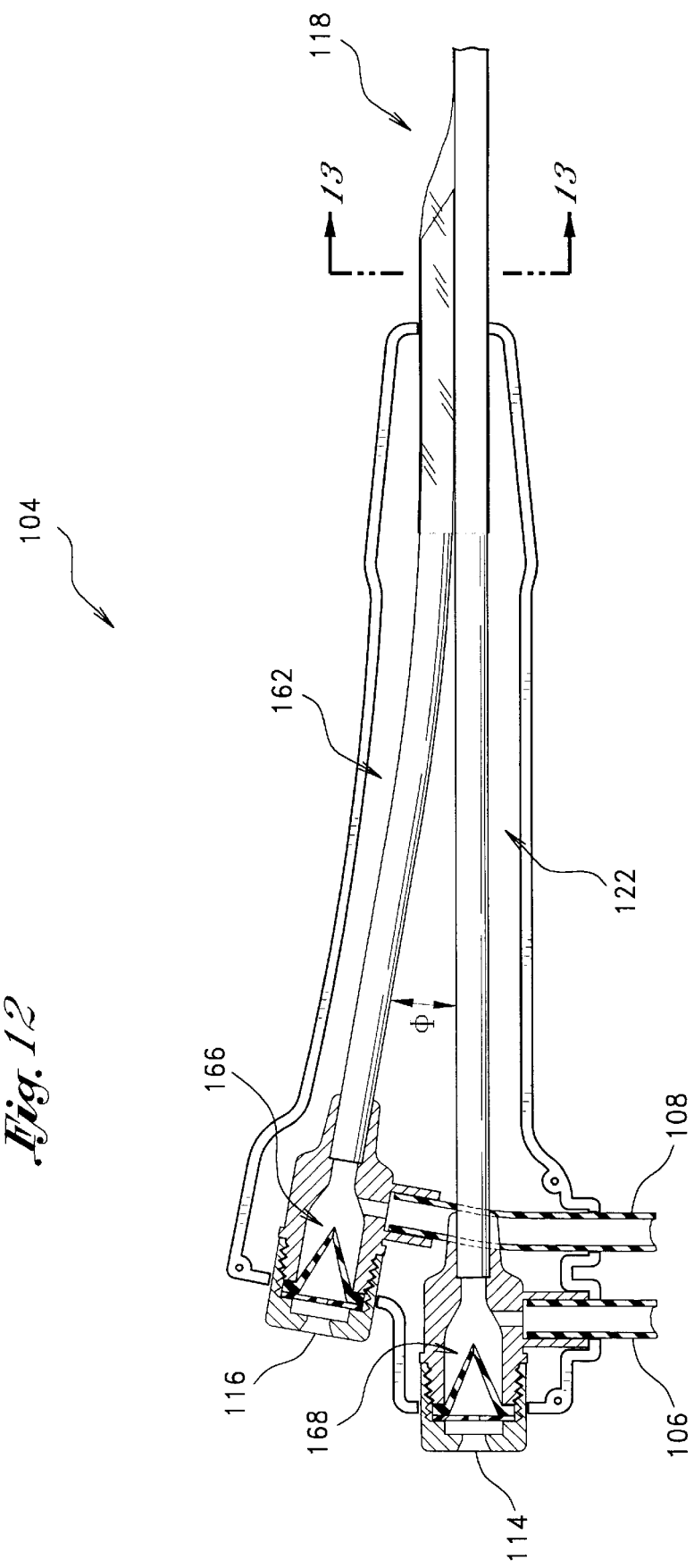

SURGICAL ACCESS DEVICE AND METHOD OF CONSTRUCTING SAME

FIELD OF THE INVENTION

The present invention relates generally to surgical access devices for use in endoscopic surgery, such devices comprising introducers, endoscopic sheaths, catheters, endoscopes, cannulas, and the like, and, more particularly, to surgical access devices having secondary channels for the post-introduction insertion of endoscopic surgical instruments, and to a method for constructing such channels.

BACKGROUND OF THE INVENTION

The advantages of minimally invasive surgery are well known and understood. Essentially, through the use of advanced endoscopy and other vision systems, surgery can be performed percutaneously through one or more small incisions or portals formed in the patient's body or through a bodily orifice, such as vagina, cervix, urethra, rectum, mouth, etc. Entrance to the body is accomplished in a number of ways depending upon the type of procedure. Once a portal or "port" is formed in the patient's body, a number of surgical access devices may be placed therethrough in order to perform the endoscopic procedure. Such devices will typically include some form of endoscope or other vision system to allow the surgeon to visualize the procedure. However, other surgical access devices may be used in combination with an endoscope, such as an introducer, an endoscopic sheath, catheters, or other cannulas. Thus, endoscopes and other endoscopic surgical instruments may be inserted through these surgical access devices which may have one or more instrument channels formed therein. Such surgical access devices may be reusable and, thus, require sterilization (such as most endoscopes), or may be disposable (such as introducers, endoscopic sheaths, etc.).

Minimally invasive surgery obviously reduces the trauma and pain to the patient, accelerates recovery, and shortens the average hospital stay, thus minimizing the costs of health care in the U.S. and around the world. In addition to minimal invasiveness, there is also a trend to attempt to perform unanticipated procedures during the initial surgery so as to avoid scheduling repetitive surgeries. That is, for example, frequently a diagnostic procedure is scheduled for a given purpose; however, once inside the patient, the surgeon notices a cyst, polyp, lesion, or other suspicious pathology. Therefore, the surgeon may desire to perform a biopsy or other surgical procedure. If an additional diagnostic or therapeutic procedure could be accomplished concurrently with the initial procedure, substantial savings in patient comfort, recovery time, and costs could be realized. However, presently in most cases, the patient must be rescheduled for a later procedure.

Although it is known in the prior art to provide auxiliary, expandable channels in surgical access devices, they have apparently not met with commercial success. A number of reasons may be postulated.

Although it is understood that the surgical access device must initially have a small cross-sectional profile for ease of insertion, the means for expanding that device have varied. Typically, such expansion means comprises a secondary or auxiliary channel having a lumen for the insertion of an endoscope or other endoscopic instrument. Thus, the main lumen of the surgical access device is formed by a hollow channel defined by a certain wall of thickness. The cross-sectional profile of the surgical access device is usually circular, although other profiles have been utilized. As used herein, "profile" will mean a cross-sectional profile unless otherwise specified. Thus, the goal of present access devices is to minimize their profile upon initial introduction. Following insertion, however, it is desirable to form a secondary channel in the device for the insertion of a second instrument in order to complete the intended procedure or another unanticipated procedure. This secondary channel is typically formed from a polymeric or rubberized elastic material. Due to their elastic nature, such secondary channels have substantial wall thicknesses. Moreover, in order to minimize the profile of the device upon insertion, these secondary channels must be collapsed in some fashion upon insertion. Thus, the cross-sectional wall thickness of the secondary channel must lie upon the outer diameter of the main channel, thus adding significantly to the overall profile of previous surgical access devices. This construction adds a new problem to the one the device is attempting to solve.

The most commonly proposed solution to the extra profile added by the secondary channel, is to surround it with an outer sheath or other elastic band, in order to hold it in a collapsed state around the outer diameter of the main channel of the surgical access device. However, this approach simply aggravates the problem due to the wall thickness of the outer sheath or banding. Moreover, these outer materials add to the radial resistance which must be overcome in order to push the instrument through the secondary channel. In addition, and quite significantly, the elastic nature of previous secondary channels presents severe frictional disadvantages, further intensifying the problem of instrument insertion. Moreover, in reusable systems, the outer sheathing or banding, which causes a secondary lumen to collapse, presents a substantial problem with respect to sterilization.

Another significant disadvantage of prior secondary channels is that they are elastically expandable, both longitudinally and radially. Thus, upon either insertion and/or deployment of secondary instrument, the channels may become loose or gathered. Thus, upon insertion of the instrument, there might be bunching or binding, which prevents the instrument from smoothly accessing its desired location. This requires the application of greater force on the instrument, thus increasing the pain and trauma to the patient which is intended to be avoided by the surgical access device. That is, most procedures of this type are performed on an out-patient basis with the patient undergoing only a local anesthetic. Thus, the difficulties associated with previous secondary channels, including their more frictional nature, increases the likelihood that the procedure will be uncomfortable and even traumatic for the patient.

Moreover, because of the elastic nature of previous secondary channels, they require an additional hollow tube to hold them in the open position for repetitive instrument insertion. Furthermore, there has been a lack of attention to leading edge design, so as to avoid contamination upon insertion of prior art surgical access devices. This is particularly a severe problem in connection with the usable systems which require sterilization between use.

Thus, there are substantial problems associated with secondary channels formed in a prior art surgical access devices. Moreover, previous devices have not addressed advances in endoscopic design. That is, initially endoscopes were of the straight and rigid rod lens type, or the more costly flexible scopes with articulating distal ends. However, more recent semi-rigid endoscopes are smaller in diameter and allow some flexibility in use, unlike rigid scopes. Semi-rigid endoscopes present new obstacles, but also additional opportunities, with respect to auxiliary channels, which opportunities have not been addressed by previous surgical access devices.

Accordingly, there is a severe need in the prior art for surgical access devices and methods for constructing them which can successfully provide secondary or auxiliary surgical channels.

SUMMARY OF THE INVENTION

The present invention satisfies this need in the prior art by providing a surgical access device and method of constructing same wherein the secondary or auxiliary lumen comprises a guide channel formed from an extremely thin, but very strong and substantially noncompliant membrane. This guide membrane exhibits performance characteristics which make it preferred for this application.

The wall thickness of the membrane is so thin (approximately 0.001 inches in some embodiments) that it has only a negligible affect on the profile of the present surgical access device. This is true even though the membrane may be pleated, folded, or doubled back on or around the outer wall surface of the surgical access device. Thus, the guide membrane of the present invention is compatible with very small diameter access devices which are more commonly being used with rigid and especially semi-rigid endoscopes. Accordingly, the surgical access device of the present invention is able to substantially reduce the pain and trauma associated with endoscopic procedures.

One important advantage of the present membrane is that it can be formed or set in position on the surgical access device. That is, by the use of heat-forming or heat-shrinking techniques, or other mechanical or chemical (e.g., adhesives) means, the membrane can be "set" in order to closely conform to the outer surface configuration of the access device, thus maintaining a narrow or otherwise small profile. Moreover, outer elastic sheathing, straps, or binding of any type are unnecessary; thus, the profile of the access device is further minimized. An additional advantage of the present membrane is its lubricity. That is, the material in its natural state as formed on the access device is lubricous or otherwise less-adhesive, thereby facilitating inserting of the access device and reducing discomfort.

The guide channel membrane of the present invention can be constructed from any one of a number of highly oriented or cross-linked, noncompliant materials, including, without limitation, polymers. Such polymers may preferably undergo an extrusion process in order to achieve their high orientation status, resulting in their noncompliant and substantially inelastic nature. Moreover, such extruded polymers are also very strong and tough, and lubricous as pointed out above. In the preferred embodiment, one guide channel membrane material is polyethylene terephthalate ("PET"); although other materials within that group are possible, examples being polyolefins and their blends which can be highly orientated or cross-linked after radiation treatment and heat forming as found in the art of balloons for angioplasty catheters. Other materials include nylon and polyethylene which achieve orientation by pre-stretching whereby the material has high strength and little elongation when a load (stress) is exerted upon it.

The guide channel membrane may be formed from material having various thicknesses, depending upon the application of the particular surgical access device; however, thicknesses in the range of 0.0005–0.002 inches are preferred. Thus, it can be seen that such membranes do not add significantly to the profile of the access device.

Another advantage of the guide channel membrane of the present invention is that they are "releasable" upon dilation. That is, although heat formed or otherwise set so as to closely conform to the outer configuration of the access device, the membrane material can easily open up or release to form a secondary guide channel. In most cases, dilation can be achieved by the secondary endoscopic instrument itself, without a need for a dilator or obturator. Thus, these additional steps can be avoided. Moreover, the materials are also internally lubricous, thus, minimizing resistance to instrument insertion and advancement. The lubricous nature can also eliminate the need for additional layers of material, such as Teflon and their coatings, which can add profile as well as cost to the device. Since the membrane material is not elastic and is otherwise releasable, there is no radial resistance to instrument advancement. In addition, no internal support is necessary. That is, once the membrane material has been released, it forms a secondary channel which conforms to the nature of the tissue around it. In other words, if the tissue surrounding the access device and secondary channel is tight, the membrane will collapse and conform at the tissue in order to avoid unnecessary trauma. On the other hand, if the passage is expanded or dilated, the channel, following release, will maintain its general channel-like shape, without the need for any auxiliary internal tubing or support from any media such as fluid. Thus, the membrane will maintain its configuration even with the instrument removed.

The guide channel of the present invention is self-adjusting. That is, the membrane material will release to form a secondary channel which is only large enough to admit the passage of the instrument being advanced through it. Thus, the guide channel holds the instrument securely along its path as it is advanced to the distal end of the access device. This advantage also allows for insertion of instruments having various cross-sectional profiles, thus avoiding the need to design secondary channels specifically for certain instruments. In certain embodiments, perforations or slits may be formed in the guide channel in order to facilitate release or dilation.

As noted above, the guide channel membrane is distensible, but substantially noncompliant. Thus, it will not expand elastically upon insertion or dilation, either longitudinally or radially. It will be understood that the term "radially" is intended to mean in an outward direction, the cross-sectional configuration of the present guide channel not being limited to a circular or cylindrical configuration. Thus, the guide channel will not bunch up or bind as the instrument is advanced through it. Moreover, because of its toughness and strength, repetitive insertions of the instrument without failure are readily achievable, especially in tight or strong tissue, such as experienced in laparoscopic applications. In addition, the membrane under these conditions will not experience longitudinal expansion, which could result in the guide channel extending beyond the distal end of the introducer, thereby blocking or obscuring vision of the endoscope.

Upon withdrawal, the guide channel membrane is easily collapsible so as to minimize any pain or trauma. Moreover, with the application of a slight vacuum, the membrane will conform closely to the outer surface configuration of the surgical access device for easy withdrawal.

The surgical access device of the present invention can be constructed from inexpensive materials and in accordance with simple construction techniques. This is particularly true of the guide channel membrane. Thus, the access device is disposable, thus avoiding problems associated with sterilization. Moreover, the membrane is compatible with any type of surgical access device, including introducers, endoscopic sheaths, catheters, cannulas, and endoscopes themselves.

In accordance with another advantage of the present invention, one embodiment of the membrane described above is used to form a guide channel on the surgical access device. Unlike secondary channels of the prior art, the present guide channel can be used to guide an instrument through a bend or curve as may be experienced in a procedure using a semi-rigid endoscope. In other words, such endoscopes are often used in connection with curved introducers which allow them to navigate certain curved anatomical paths and/or to move or visualize tissue. Thus, in accordance with one aspect of the present invention, the guide channel is nonlinear. Such a channel can be formed upon a guide platform which is formed on or is otherwise associated with the access device. Moreover, guide rails can be formed to further provide structure and rigidity to the secondary channel. The bends or curves formed in the guide channel to orient the secondary lumen so that the instrument can arrive at a specific distal location with respect to the primary lumen, depending upon the procedure.

The guide platforms or rails can take on a number of configurations. Advantageously, however, due to the formable and thermoplastically settable nature of the channel membrane, the channel membrane can be folded or arranged with respect to the access device in a wide variety of ways.

The surgical access device of the present invention also exhibits a particular distal end design which avoids contamination. Upon insertion of the device, the instrument channel is sealed so as to avoid entry of tissue or foreign contaminating material. Due to the thermoplastic nature of the channel membrane, the seal can be accomplished by heat forming the channel at the distal tip. Alternatively, a narrow profile tip can be designed which plugs the distal opening of the secondary channel while still facilitating entry of the access device. Like the distal end of the present access device, the proximal end also features a particular "y" design which facilitates advancement of a secondary instrument into the guide channel while minimizing risk of damage to the device or discomfort to the patient. The proximal end of the access device is provided with a housing which gently introduces the instrument along a path which eventually becomes tangential to the main longitudinal axis of the access device. The housing which surrounds the proximal end is also provided with appropriate valves to control and regulate the in-flow and out-flow of distension media, irrigation fluid, or other fluid.

As noted above, the guide channel of the present invention can be integrally formed on the insertion tube of an endoscope or separately formed on an introducer, endoscopic sheath, and the like. In the latter case, the introducer can be designed and constructed so as to guide the entrance of the secondary instrument in a particular way in order to achieve a specific purpose, depending upon the procedure being accomplished. Moreover, the instrument can enjoy a lumen independent of any movement of the endoscope which is inserted through the main channel of the introducer.

In accordance with the method of construction of the surgical access device of the present invention, as noted above, the settable nature of the membrane material facilitates a number of construction arrangements and techniques. Thus, the membrane material can be folded or stored with respect to the access device on an exterior surface, interior surface, or other intermediate location. It can be coupled to the access device by a wide variety of means, including mechanical, adhesive, heat formation, etc.

Thus, in accordance with a preferred method, the surgical access device of the present invention is constructed from a main tube which provides a main channel for the access device. The main tube can be constructed from stainless steel tubing or a rigid plastic such as polycarbonate which can provide strength with little wall thickness. Typically, the main channel provides access for insertion or introduction of an endoscope; however, other instruments can be introduced into the patient as well through the main channel. The guide channel membrane is formed onto the main tube in the following manner. The membrane is provided in the form of a hollow tube, which is typically extruded to form that shape, so as to have an outer diameter which is greater than that of the main tube. The membranes can be constructed from PET tubing which can come in the form of balloon tubing which is pre-stretched and highly orientated for minimal elongation. Other constructions of membranes can use polyolefins and their blends, polyethylene, and nylons which are highly orientated or cross-linked. The guide channel membrane tube is placed over the main channel tube and positioned eccentrically with respect to the axis thereof.

A split tube sheath is mechanically clamped over the main tube capturing the guide channel membrane tube against the main tube. The split tube can be made from nylon 11 which has high strength with little wall thickness. Other materials such as polycarbonate, polyethylene, urethane, and the like can be employed. The split channel can be mechanically affixed to the main tube or be placed onto the main tube by a variety of adhesive agents or thermal bonding techniques. The actual width of the slit itself can vary which will affect the profile and guiding characteristics of the membrane channel. The excess membrane material, owing to the fact that its outer diameter is greater than that of the main tube, is allowed to escape through the slit in the sheath and extends outwardly therefrom. This excess material is then folded, pleated, or otherwise stored with respect to the main tube in any one of a variety of ways so as to minimize the profile of the surgical access device. Typically, the excess membrane material is folded or doubled back on itself so as to closely conform to the outer surface configuration of the tube. An intermediate amount of heat, such as approximately 160° F., is then applied to the membrane material so as to heat form or set it in position closely conforming to the main tube, although other mechanical forming or adhesive techniques may be employed. The settable nature of the membrane is such that a crease or seam formed in the pleated material will retain a sharp, narrow profile, thus facilitating entry and use and avoiding damage or distortion to the guide channel under these conditions.

In accordance with another method of construction and introducer embodiment, an even narrower profile introducer can be constructed without the need for an outer split sheath. In this case the guide channel membrane tube is heat bonded or otherwise coupled directly to the hypotube by adhesive or other means. To facilitate this construction, the membrane tube can be supplied in a multi-lumen or figure-8 configuration, wherein the membrane is constructed from an extrusion or other process. Moreover, one or more of the lumens may be collapsible, and the others may be noncollapsible, either due to their increased wall thickness or to rigidifying means such as hypotubes or reinforcement devices, etc.

In accordance with another step of the present method, a merge channel may be formed along the main channel in order to provide for the easy insertion of a secondary instrument into the guide channel. The merge channel can be constructed from a variety of materials including nylon 11 and other polymers as well as stainless steel which can be flexed yet retain radial integrity. As noted above, the merge channel is proximally located with respect to the surgical access device and remains substantially out of the body. In accordance with the present method, the merge channel tube is longitudinally aligned with respect to the axis of the main tube prior to the over-wrapping of the guide channel membrane tube. Thus, the proximal end of the membrane tube circumscribes both the main tube and the distal end of the merge channel tube and the guide channel is simultaneously formed around both the main tube and the merge channel tube to comprise the "y" junction of the surgical access device. To provide mechanical strength at this "y" junction, a housing or other mechanical clamping means is provided. The housing can take a variety of forms to provide ergonomic benefits to the operator or clinician. In construction, it can be made from a variety of injection molded plastics including polycarbonate, polysulfone, nylon, etc., or machined. It can be a part of the disposable introducer or a separate unit which is reusable, re-sterilized, and placed back onto the surgical access device by the operator prior to each use.

In another step of the present invention, the distal tip of the surgical device is sealed so as to prevent contamination or distortion of the guide channel upon insertion of the access device into the body. Likewise, at the proximal end of the access device, the main channel and merge channel are provided with the necessary valving for irrigation or distention media. The valving must prevent any leakage around an instrument or endoscope when these devices are placed through the ports and typically has an O-ring or washer type structure. In addition, they must contain structures such as duck-bill or star valves which prevent the back flow of media through the ports when no instrument or endoscope is through the port. These valves can be made from silicone, rubber, and other elastomeric materials which are known in the art.

Thus, in summary, the surgical access device of the present invention comprises a first channel having a first lumen for the insertion of an instrument, endoscope, or other visualization device, and at least one secondary channel for providing an auxiliary lumen for the insertion of an instrument, endoscope, or other visualization device, wherein the secondary channel is mounted along the outer surface of the surgical access device and is constructed from a thin pleated membrane which, prior to dilation of said secondary channel, so closely conforms to the outer surface of the device so as to only negligibly increase the size of the profile of the device. The present invention further comprises a surgical access device as described above, wherein the secondary channel is constructed from a membrane which is self-conformable to the device and which is settable, so as to closely conform to the surgical access device.

Accordingly, a surgical access device of the present invention and the method of constructing it provide a substantial advancement over the prior art.

BRIEF DESCRIPTION OF THE DRAWINGS

FIG. 3 is a cross-sectional view of the access device taken along line 3—3 of FIG. 2 illustrating the main channel and guide channel in their initial state upon insertion of the access device into the body and prior to deployment of a secondary instrument through the guide channel.

FIG. 3a is a cross-sectional view of the access device illustrating an alternative embodiment of the main channel and guide channel prior to deployment of a secondary instrument through the guide channel.

FIG. 3b is a cross-sectional view of the present access device illustrating an alternative embodiment for the guide channel which does not utilize a split sheath.

FIG. 3c is a cross-sectional view of the access device of FIG. 3b, illustrating the guide channel in its deployed or released position.

FIG. 4 is a cross-sectional view of the access device taken along lines 4—4 of FIG. 2 illustrating the guide channel of the present invention in a released or expanded state as the secondary instrument is advanced therethrough.

FIG. 10a is the guide channel embodiment of FIG. 10 with an instrument deployed substantially along the length of the guide channel.

FIG. 12 is a longitudinal cross-sectional view taken through the proximal housing of the present access device in order to illustrate the merge channel leading into the guide channel of the present invention.

DETAILED DESCRIPTION OF THE PREFERRED EMBODIMENT

Figure 1:
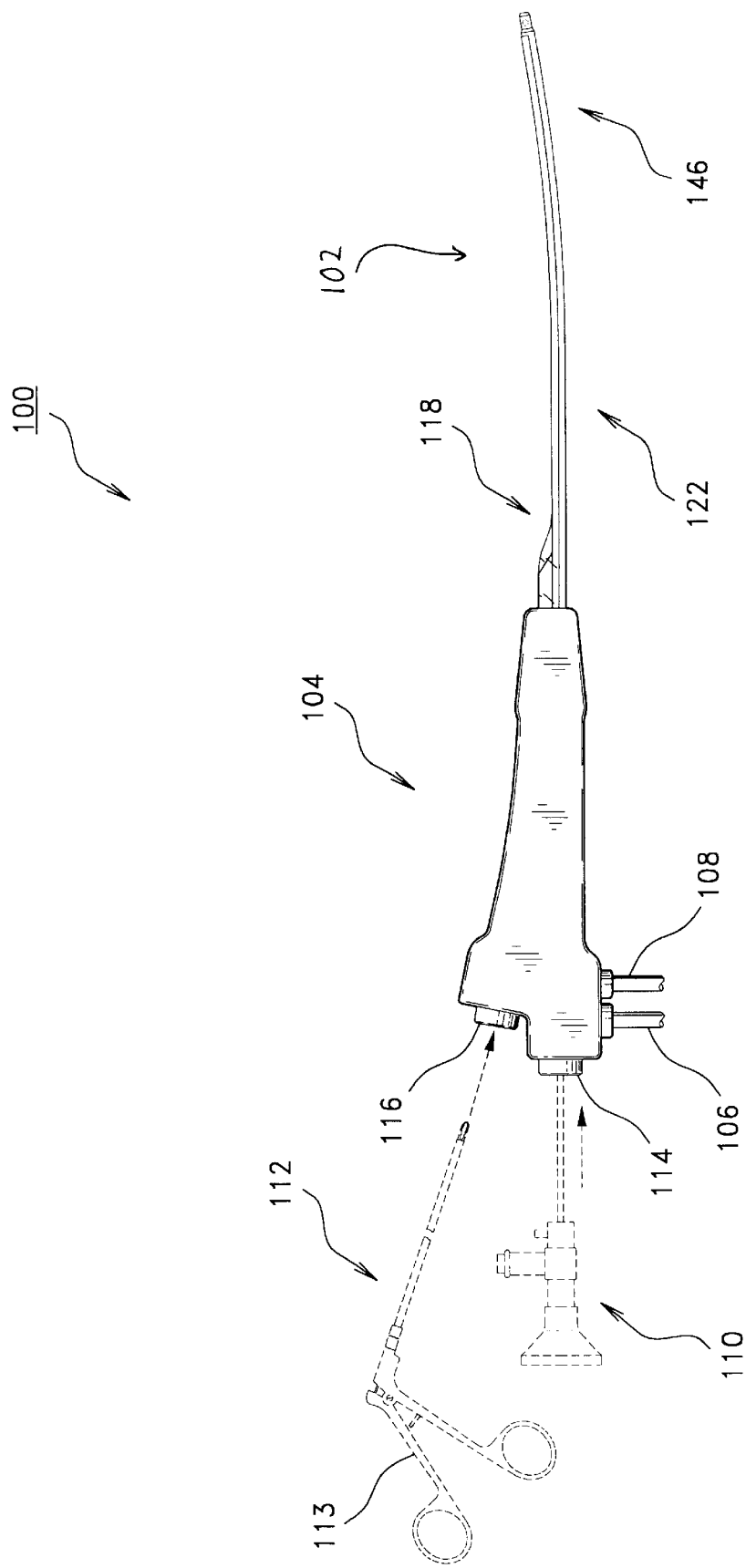
FIG. 1 is a side view of the surgical access device of the present invention illustrating a partially inserted endoscope and a secondary instrument in a pre-introduction location.

With reference to FIG. 1, there is shown the surgical access device 100 of the present invention. In this case, a surgical introducer has been selected to illustrate the principles of the present invention; however, it will be understood that such principles apply equally to all types of surgical access devices, as well as to devices not necessarily limited to surgical access. In the broadest sense, the principles of the present invention encompass devices where secondary channels or other types of guide channels, expandable or otherwise, are desirable or necessary in order to allow passage of some type of instrument. Such devices include, without limitation, introducers, endoscopic sheaths, catheters, cannulas, and the like. The secondary or guide channels of the present invention may be retro-fitted onto such devices or integrally formed therein For example, the guide channel of the present invention may be integrated into the insertion tube of an endoscope itself.

Furthermore, it will be understood that the present invention is compatible with all types of instruments, including catheters, obturators, etc. Also, visualization devices used with the present access device are not to be limited to endoscopes, but also include all types of such devices, including fluoroscopes, etc. Thus, the terms "instrument" and "endoscope" are intended to be only illustrative and representative of the wide variety of devices that can be utilized in accordance with the present invention, and such terms are not intended to be limiting in any respect.

Thus, the fact that the present invention is described with respect to an introducer is illustrative only and not intended to be limiting in any respect.

Surgical Introducer

Thus, with further reference to FIG. 1, there is illustrated a surgical introducer 100 into which the principles of the present invention have been incorporated. In this case, the introducer 100 is intended for gynecological procedures, such as hysteroscopy or cystoscopy; however, again, a wide variety of procedures may be performed with the surgical access device 100 of the present invention.

As shown in FIG. 1, the access device 100 comprises a distal insertion portion 102, which is intended for insertion into the patient's body, and a proximal housing portion 104, which generally remains outside of the patient's body. In this case, access to the patient's body is achieved through dilation of the cervix; however, in other procedures, access may be gained through other natural openings in the body or by surgical incision, etc. The details of construction of the insertion portion 102 are described below in more detail and illustrated in connection with FIGS. 3 and 4, while the details of the housing portion 104, including in-flow and out-flow conduits 106, 108, are described and illustrated below in connection with FIG. 12.

To the left of the proximal housing portion 104 as shown in FIG. 1, there is shown in exploded relationship to the introducer 100 an endoscope 110 and a secondary instrument 112, in this case a grasper which can be used for the removal of foreign bodies or tissue. The endoscope 110 is shown partially inserted into a main or endoscopic port 114 formed at the proximal end of the introducer 100. The secondary instrument 112 is shown positioned prior to insertion into a secondary or instrument port 116. The terminology of main or endoscopic port 114 and secondary or instrument port 116 is merely illustrative since the endoscope 110 is typically inserted into the main port 114 of the introducer 100, while the secondary instrument 112 is inserted through the secondary port 116. However, in accordance with the principles of the present invention, this arrangement can be reversed, or any other of a wide variety of instruments may be used in connection with the various ports of the access device. In addition, multiple ports in addition to two may be formed on the introducer 100, depending upon the nature of the procedure to be performed.

FIG. 1 illustrates the introducer 100 prior to and upon insertion into the patient's body, but prior to insertion of any secondary instrument. Although not readily apparent from FIG. 1, a guide channel 118 of the present invention is mounted and formed on an exterior surface 120 of the endoscopic channel 122 which forms the basic cross-sectional profile of the insertion portion 102 of the introducer 100. Since the secondary instrument 112 has not yet been inserted through the instrument port 116 or through the proximal housing 104 to the insertion portion 102, the guide channel 118 for the instrument is virtually unnoticeable to the eye or touch. Thus, as illustrated in FIG. 1, the guide channel 118 adds only a negligible dimension to the profile of the access device 100, thus minimizing pain and discomfort to the patient. This a particular advantage in gynecological procedures which are frequently performed on an out-patient basis and under only a local anesthetic. Thus, if a secondary procedure proves unnecessary, there has been no unnecessary discomfort or pain to the patient since the profile of the introducer 100 has been minimized. However, if such a secondary procedure becomes necessary, it can be readily accomplished with only a minimal intrusion into the body through the existing port, without the need to schedule a second surgery. It also has the obvious advantage of not requiring a pre-dilatation step prior to the insertion of the introducer 100. In some cases, such as for the cervix, dilatation of the cervical canal can be painful to the patient and should be minimized as much as possible. In addition, the uterine cavity requires distension to allow for proper visualization. If the cervix is over dilated during the pre-dilatation step, excessive cervical leakage can occur when trying to distend the uterus. Thus, the introducer 100 with its guide channel 118 and low profile will minimize pre-dilatation of the cervix and will provide a guide channel 118 with the diameter of the instrument being used, thereby reducing the leakage potential via an overly dilated cervical canal.

It will be noted from FIG. 1 that the guide channel 118 closely conforms to the outer configuration of the endoscopic channel 122 without the need for outer sheaths or bands which would increase the profile thereof. Moreover, since the guide channel 118 is formed on the exterior 120 of the endoscopic channel 122, its natural lubricity provides an important advantage in connection with the ease of insertion of the introducer 100. However, it will be noted in accordance with the present invention that the guide channel 118 may also be formed on or within the endoscopic channel 122 in other configurations with respect to the introducer 100. Moreover, multiple guide channels may be formed on or incorporated into the main or endoscopic channel 122.

Figure 2:
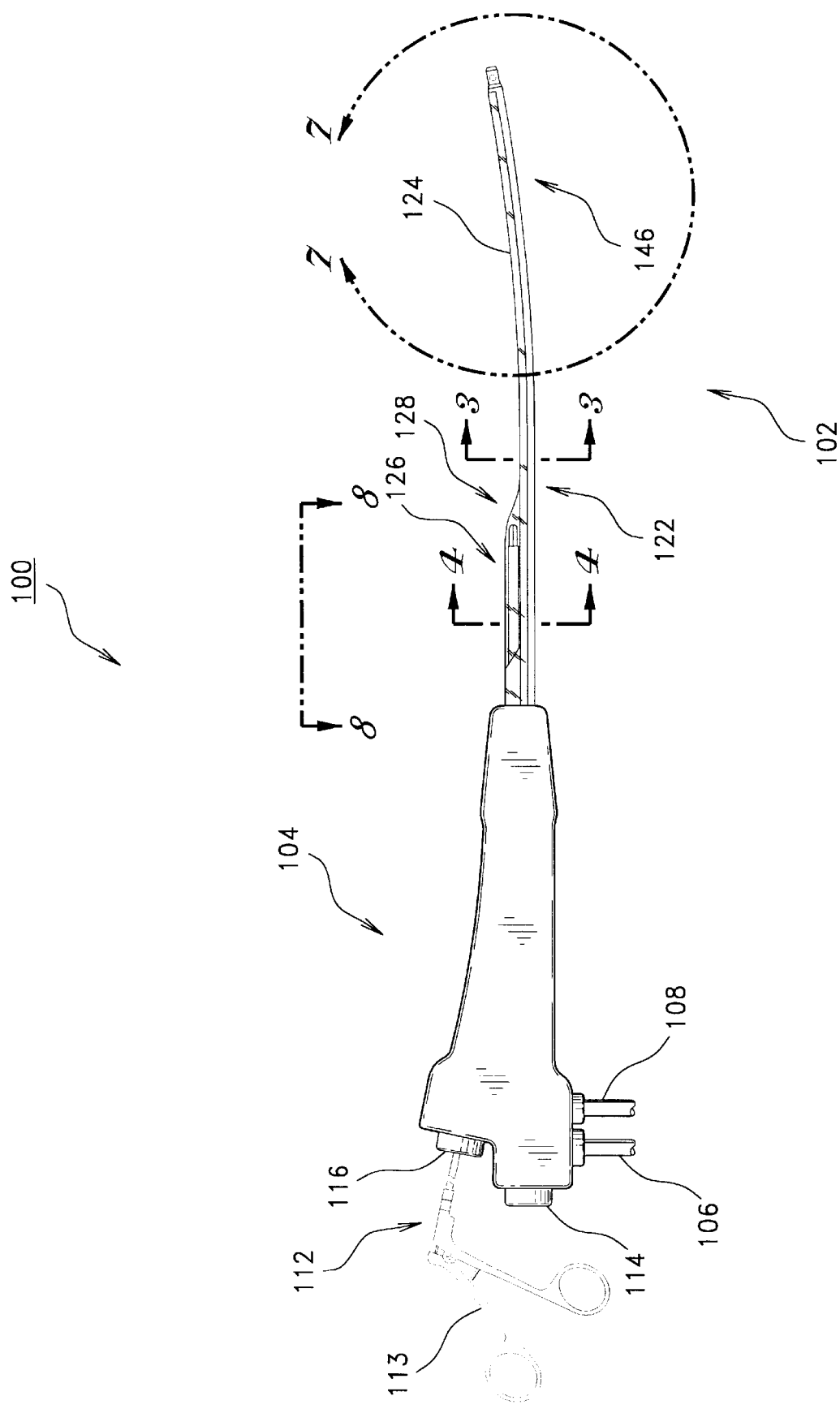
FIG. 2 is a close-up side view of the access device illustrating the advancement of the secondary instrument through the guide channel of the present invention.

FIG. 2 is a view of the introducer 100 of the present invention illustrating the deployment of the secondary instrument 112 as it advances along the guide channel 118. In this FIG. 2, the guide channel portion 124 ahead of the instrument 112 is folded over and upon the insertion portion 102 of the introducer 100. The characteristics of the guide channel 118 at this location are described below in more detail in connection with the description of FIG. 3. However, in the region of a leading edge 126 of the instrument, a guide channel portion 128 is shown to be releasing its insertion position and gradually expanding so as to allow the instrument 112 to advance. It will be noted that, although FIG. 2 shows expansion or dilation to be achievable by the use of the secondary instrument itself, other instruments, hollow tubings, media, or means are equally available to achieve expansion in accordance with the guide channel 118 of the present invention.

As the instrument 112 advances, the guide channel 118 gradually releases in order to maintain the minimum profile of the introducer 100. Thus, pain and discomfort to the patient are minimized. Furthermore, the surgical access device 100 of the present invention makes it possible for more endoscopic surgical procedures to be conducted on an out-patient basis with only minimal or local anesthesia.

Such procedures would include those which are planned and scheduled, as well as secondary procedures which are unanticipated. In other words, a surgeon may enter a patient's body endoscopically for the purpose of a particular, planned diagnostic or therapeutic purpose. Initial insertion of the introducer 100 is typically accomplished under the visual guidance of the endoscope 110. However, once inside the patient's body, under these visual conditions, it may become necessary or desirable to perform a secondary procedure using a secondary instrument 112 inserted through the instrument port 116 and advanced through the proximal housing portion 104 and into the guide channel 118 of the present invention. Thus, regardless of the initial purpose of the endoscopic procedure, this secondary procedure can be performed virtually simultaneously without rescheduling a second procedure. Moreover, the secondary procedure can be performed with only minimal discomfort to the patient and without withdrawing or reinserting the endoscope or any other instruments. Because of the narrow profile of the present access device 100, a wide variety of primary and secondary endoscopic procedures (as well as multiple procedures of all types) can be safely and efficiently performed on an out-patient basis. Thus, the high cost of health care can be contained somewhat.

Guide Channel

An important feature of the present invention which allows these advantages to accrue is the guide channel 118 of the introducer 100. This guide channel 118 can be described in more detail in connection with the cross-sectional drawings of FIGS. 3 and 4. FIG. 3 is a cross-sectional view of the insertion portion 102 of the introducer 100 at a location ahead of the advancing instrument 112. FIG. 3 illustrates the main or endoscopic lumen 130 for the insertion of the endoscope 110 or other instrument (although, the endoscope 110 is not shown in FIG. 3 for clarity of illustration). This lumen 130 is formed by the endoscopic channel 122 which may comprise a tube 132 of various constructions. The endoscopic tube 132 is in turn surrounded by a larger diameter split tube or sheath 134. The split in the sheath 134 defines a slit or longitudinal opening 136. Sandwiched between the inner endoscopic tube 132 and the outer split sheath 134 is a membrane 140 which forms the present guide channel 118. This membrane 140 can initially be formed in the shape of a tube or other construction.

As shown in FIG. 3, the membrane 140 surrounds the inner endoscopic tube 132 but, due to its greater diameter, also extends out of the longitudinal opening 136 in the split sheath 134. This excess membrane material may be folded back onto the outer surface 120 of the split sheath 134 to form a double-layer of the membrane 140 along a partial circumference of the introducer 100.

This folded-back portion 124 shown in FIG. 3, forming pleats 123, 125, is that portion which defines the guide channel 118 for the instrument 112, as illustrated in more detail in FIGS. 2 and 4. However, as illustrated in FIG. 3, prior to instrument deployment, the guide channel 118 is defined by a membrane which closely conforms to the outer surface 120 of the split sheath 134. For example, the lateral edges of the pleats 123, 125 can be provided with thin creases or seams 127, 129, which can be formed and set in the membrane material. Thus, the narrow profile of the introducer 100 is maintained. In addition, because of the close conformity of the guide channel membrane 140, it is less likely to be distorted or disturbed upon insertion of the introducer 100 into the body. Thus, the guide channel 118 maintains its structural integrity and avoids patient discomfort even before insertion of the secondary instrument 112.

The membrane 140 which comprises the guide channel 118 can be extremely thin, ranging in thickness between 0.0005" and 0.002", preferably being about 0.001". Thus, even when doubled back on itself and lying on the outer surface 120 of the split sheath 134, the guide channel 118 adds only a negligible thickness to the profile of the surgical access device 100. Moreover, the guide channel in its pre-release position 124 shown in FIG. 3 will hold a set in this position and does not require any external elastic sheets or strapping to bind it in position on the introducer 100.

It will be understood, as noted above, that the present guide channel 118 can be formed on or in connection with surgical access devices of a wide variety. Moreover, in its pre-release position 124 (which it assumes prior to and even during insertion of the access device 100 into the body, but prior to deployment of an instrument 112 through the guide channel 118), the guide channel 118 can be stored, wrapped, or folded in a number of configurations, other than that shown in FIG. 3.

For example, FIG. 3a shows multiple pleats or folds 223, 225 of pleated portion 224 in the membrane 140 which will facilitate a larger membrane channel 118 and can follow a multitude of folding patterns which preferentially unfold upon the exerted force of the insertion element. The additional material which constitutes these multiple folds 224 will allow for larger instruments to pass through the membrane channel 118. Likewise, the folding pattern of the pleats may be such that all of the pleat is on one lateral side of the introducer or the other, rather than the two equal pleats shown in FIG. 3a.

Figure 7:
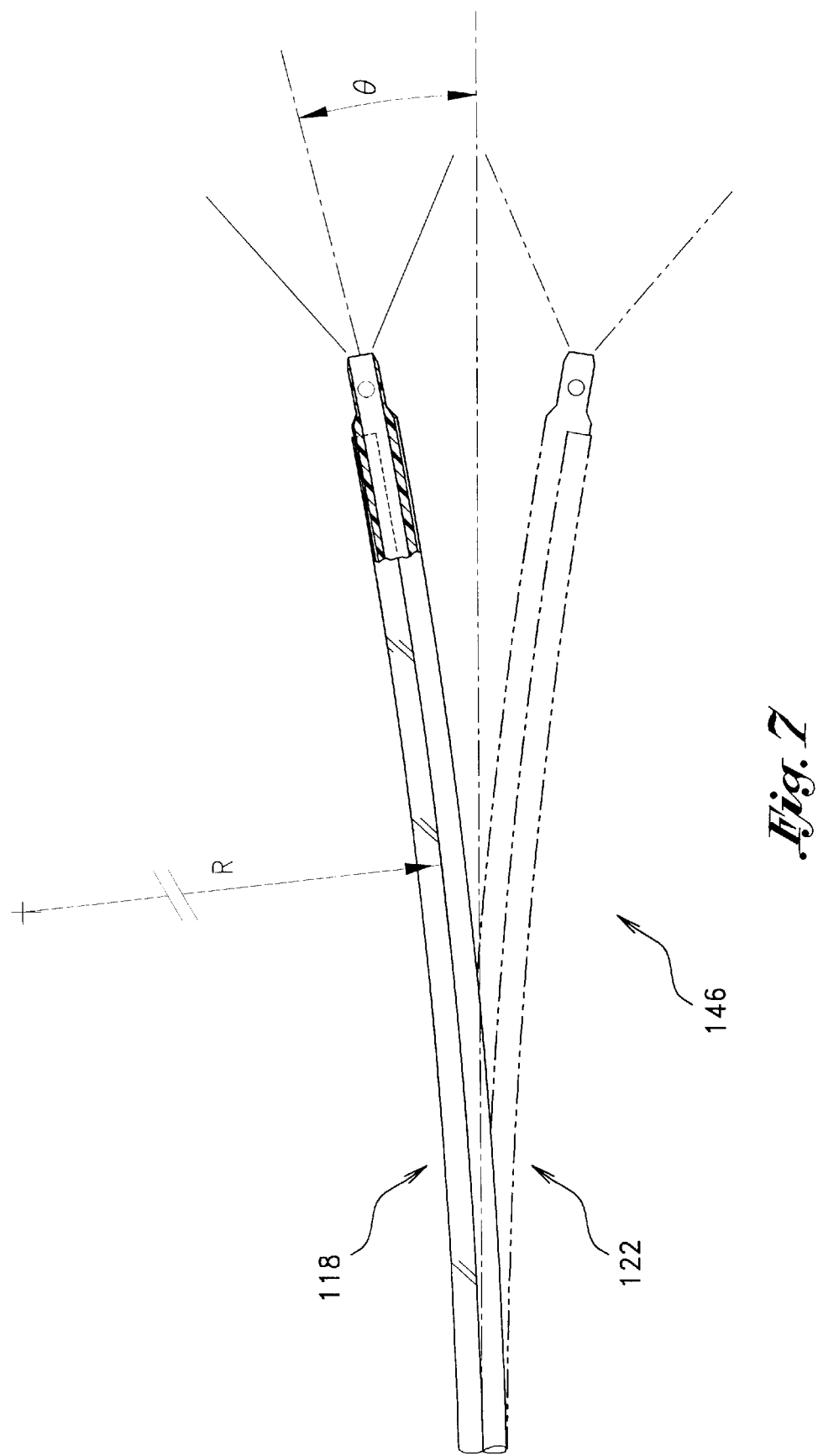
FIG. 7 is a close-up perspective view of the distal tip of the present access device illustrating a bend or nonlinear curve which may be formed in the device, and further illustrating the manner in which the present guide channel allows a secondary instrument to conform to such curve.

Although the method of construction of the introducer 100 of FIG. 2 is shown and described in more detail in connection with FIG. 14, it will be understood that the endoscopic tube 132 can be constructed from a wide variety of materials which provides rigidity and protection for the endoscope 110. Preferably, such a tube 132 can take the form of a stainless steel hypotube. Thus, the tube 132 can provide the rigidity necessary for initial insertion (especially in difficult procedures such as a laparoscopy), and can be used to move tissue without fear of damage to the endoscope 110 within. Moreover, the endoscopic tube 132 can take on a bend or curve, as illustrated in FIG. 7, to facilitate a particular procedure. With advancements in rigid and semi-rigid endoscopes, such curves or bends in introducers can facilitate intricate navigational procedures while not damaging the endoscope. The curves and bends also direct the visualization area of the endoscope to preferentially view anatomical structures not on the axis of the insertion point in the body.

The outer split sheath 134, in its typical construction, is smooth and lubricous in order to facilitate insertion of the introducer 100. It may be constructed from a durable, bio-compatible polymeric material, such as nylon. Preferably, nylon 11 can be utilized.

It will be noted in connection with FIG. 3 that typical introducer construction will include both the endoscopic tube 132 and the outer nylon layer 134. Thus, the guide channel 118 of the present invention does not significantly increase the profile of such an access device 100. In this connection, a number of cross-sectional introducer configurations will be readily apparent to those of ordinary skill in the art, including noncircular configurations. In addition, a wide variety of endoscopic tube and split sheath wall thicknesses are within the realm of the person of ordinary skill; however, preferably, the endoscopic tube 132 would have a wall thickness of approximately 0.008", while the split sheath 134 would have a wall thickness of approximately 0.005".

On the other hand, the versatility of the guide channel of the present invention allows it to be incorporated into introducers of even narrower profiles. For example, FIG. 3b illustrates a cross-sectional view of an alternate embodiment of the present introducer which does not utilize an outer split sheath to capture a guide channel membrane 340 onto a stainless steel hypotube 332. In this case the guide channel membrane 340 can be heat bonded or otherwise coupled to the tube 332 by adhesive or other means. To facilitate this construction, the guide channel membrane 340 can be supplied in a multi-lumen or figure-8 configuration, as illustrated in FIG. 3c, with one lumen 330 of the membrane 340 being mounted on the hypotube 332, leaving the second lumen 342 to be folded or pleated thereabout to provide a guide channel 324 in the stored position having pleats 323, 325. Thus, FIG. 3c illustrates this mounting position prior to the folding of the membrane 340, which position is shown in FIG. 3b. It will also be noted in connection with the embodiment of FIGS. 3b and 3c that guide channel membranes having multiple lumens can be provided and mounted on the hypotube in this or another manner, and then folded and set in position about the tube in order to provide an introducer with extremely narrow profile. Thus, three, four, or more membrane tubes can be mounted, either jointly or separately, on the introducer so as to provide multiple lumens. In addition, one or more of the tubes (which can be constructed from an extrusion or other process) may be collapsible, while others may be noncollapsible, due either to the wall thickness of the membrane extrusion or some other rigidifying or reinforcing mechanism (such as a hypotube or the like).

With reference to FIG. 4, there is shown cross-sectional view of the present introducer 100 through the insertion portion 102 where the instrument 112 has already advanced. In this case, the instrument 112 almost completely occupies a lumen 142 defined by the guide channel 118 of the present invention. As shown in FIG. 4, the guide channel 118 is shown releasing its predeployment position to allow the instrument 112 to easily pass along the guide channel 118 and into the patient.

The guide channel 118 of the present invention may be constructed from a membrane 140 which exhibits a number of advantageous characteristics. For example, in addition to its external lubricity, the membrane 140 is also internally lubricous to facilitate the deployment of the instrument 112. The physical characteristics of the membrane 140 also allow the guide channel 118 to be self-adjusting. That is, as shown in FIG. 4, the guide channel 118 releases only to the extent necessary to accommodate the particular instrument being inserted through it. If not needed, the membrane 140 remains folded in its set position in the region indicated by arrows 144 of FIG. 4. This advantageous characteristics allows the guide channel 118 to accommodate a number of instruments of various cross-sectional dimensions without significantly increasing the profile of the introducer 100.

Likewise, if the instrument 112 is removed from the guide channel 118, the membrane 140 causes it to maintain approximately the same position as it did with the instrument 112 inserted within, thus facilitating reinsertion of the same instrument or another instrument. For instance, in this case of removing multiple portions of tissue from the body, it may be necessary to remove tissue and then reinsert the instrument 112 back through the guide channel 118 to remove more tissue. Thus, there is no radial resistance to reinsertion which reduces the risk of damage to the guide channel 118 and discomfort to the patient. If the instrument 112 is withdrawn upon completion of the procedure, the guide channel 118 readily conforms to the external forces applied to it by the surrounding tissue, thereby causing the guide channel to collapse upon withdrawal of the introducer 100, so that pain or trauma to the patient is avoided. Also, if desired, the guide channel 118 can be evacuated of fluids in order to facilitate its collapse prior to withdrawal.

As noted above, the guide channel membrane 140 is noncompliant both longitudinally and radially. Thus, it does not exhibit elastic characteristics which might cause the guide channel 118 to bunch up or bind as the instrument 112 is advanced therethrough. Moreover, the guide channel membrane 140 is malleable, meaning that it tends to conform to the pressures and forces exerted upon it by ambient conditions, including anatomy, tissue, and other media. This feature advantageously tends to reduce resistance to movement of the access device 100 and enhance patient comfort. On the other hand, in the absence of such ambient forces, the membrane 140 maintains its position and configuration, having somewhat of a "memory" in this regard and exhibiting patentency characteristics. In other words, the membrane can be self-supporting, defining an instrument lumen without the need for internal wall support means.

A number of materials can achieve these advantages of the guide channel membrane 140 of the present invention. For example, inelastic polymers or other pleated, woven, or braided materials can be utilized. Preferably, however, highly orientated or cross-linked, noncompliant polymers can be utilized as a guide channel membrane material. Such materials tend to be thermoplastically settable, with glass transition temperatures greater than room temperature. In addition, such polymers are semicrystalline and deformable in the crystalline state.

These properties yield certain advantages in connection with the present invention. For example, in order to minimize profile, the guide channel membrane can be very thin, yet strong. Because the material is deformable in its crystalline state, it may be folded, pleated, rolled, or otherwise stored in combination with the introducer without the loss of its advantageous mechanical properties, such as strength, noncompliance, etc. In achieving this storage position, the membrane can readily conform to the surface or space in which it is placed. Because the membrane is thermoplastically settable, once it is stored in this position, the application of thermal energy will result in the realignment of the crystalline structure so that the membrane retains its storage position; however, it will be understood that this set in the membrane storage position can also be achieved by the application of mechanical energy or chemicals (e.g., adhesives).

Thus, it can be said that the membrane is "self-conformable," since it can conform to a surface or space and assume a given configuration, and then be self-retained in that configuration. In addition, once it is desired to remove the membrane from its stored configuration (e.g., in order to achieve dilation), its deformability is again an advantage. Besides thermal energy, mechanical, electrical, chemical, or pneumatic energy can be applied to deploy the guide channel. Again, because it is deformable in its crystalline state, it will tend to become set or retained in its deployed configuration.

One preferred polymeric example of the present guide channel membrane is polyethylene terephthalate ("PET"), although other polymers are possible. For example, polybutyl terephthalate may be utilized as a guide channel 118, as well as nylon 6 or nylon 66. These materials, as well as others, exhibit the advantages described above.

Figure 5:
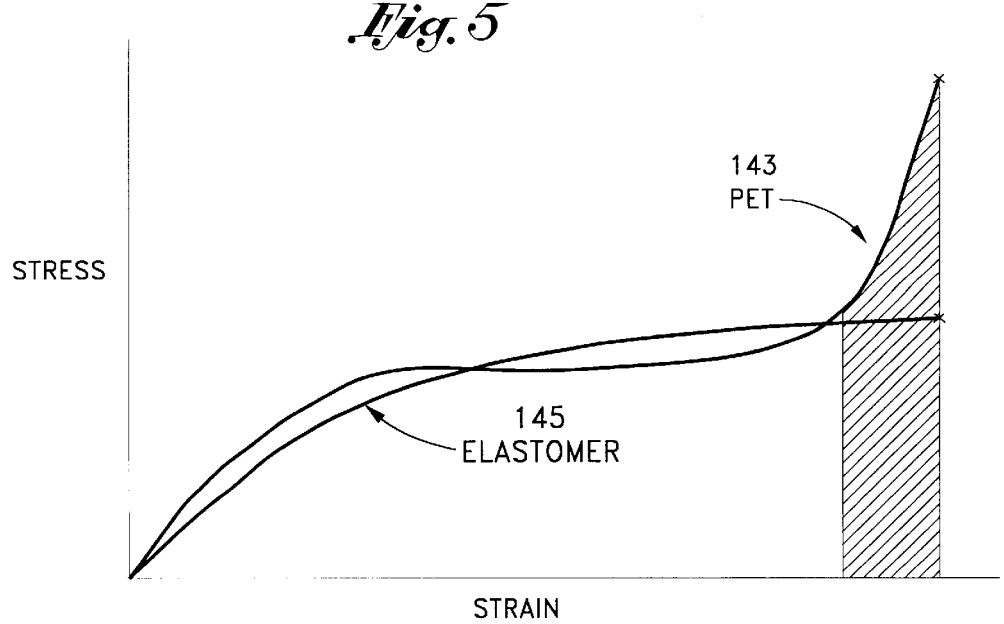
FIG. 5 is a graph illustrating the stress-strain relationship of oriented PET, as used for the guide channel membrane, in comparison with a typical elastomer.

In the case of PET, FIG. 5 illustrates the noncompliant (stress/strain relationship) of oriented PET as compared with a typical elastomer. A PET curve 143 in the graph shows a shaded region which depicts the behavior of a highly-orientated PET which has been pre-stretched. These stress-strain properties relate to a material which has high strength and very little elongation when a load is exerted upon it. Conversely, an elastomer behaves different in this and all sections of its curve 145 on the graph by elongating with little additional stress. Thus, where careful precision in the configuration of the guide channel is necessary, membrane material such as PET is advantageous.

Figure 6:
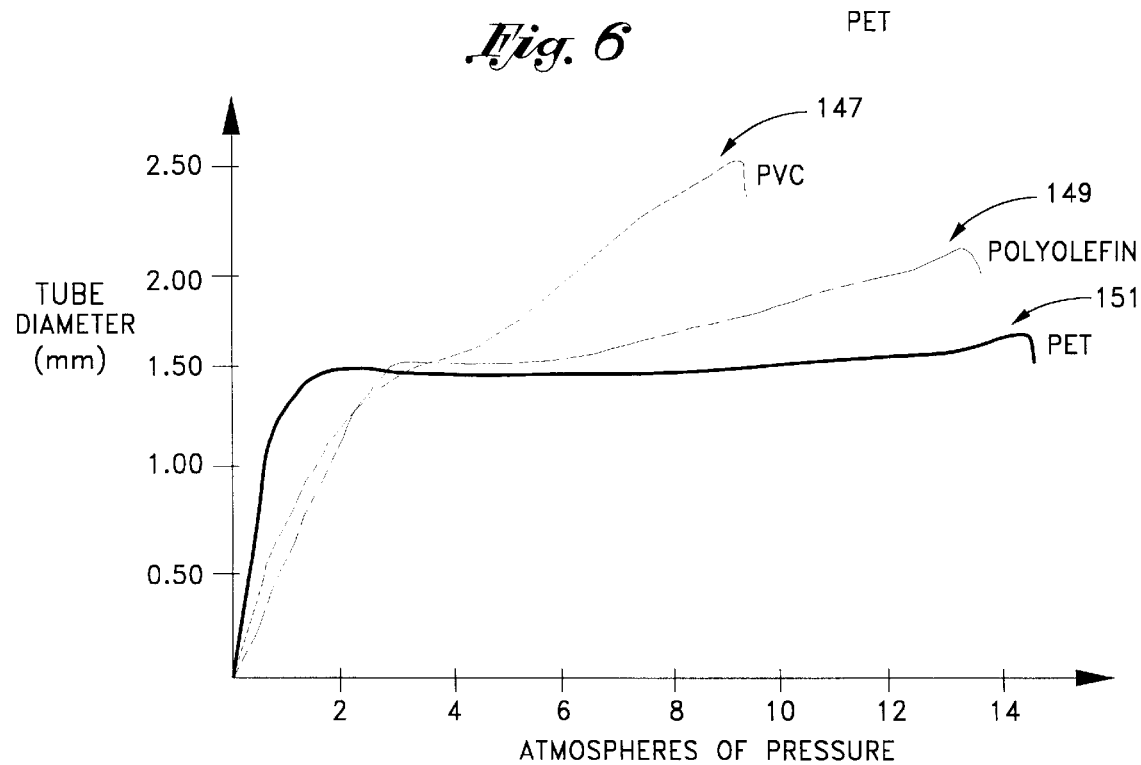
FIG. 6 is a graph illustrating the relationships between tube diameter and internal pressure for tubes comprising PVC, polyolefins, and PET material.

In addition, FIG. 6 illustrates the relationships between tube diameters and internal pressure for tubes comprising PVC 147, polyolefin 149 and PET material 151. In the graphs in FIG. 6, plots are shown for a closed vessel structure such as a balloon for various materials in which the outer diameter measurement is plotted versus the internal pressure applied. In this example, the PET material 151 demonstrates very little distension with greater internal pressure as a result of its high strength and low elongation in comparison to the polyolefin and PVC materials 149, 147 used for this example. Nevertheless, these and other materials can provide suitable guide channel membranes if treated properly during their manufacturing process. Thus, a major component of the inelastic behavior of PET and polyolefins is the fact that their polymer chains in the material have been highly orientated (PET) or cross-linked (polyolefins) with each other, providing greater strength and resistance to strain. This high degree of orientation, either by processing or secondary operations such as radiation treatment or forming and axial stretching, enables the nondistensible behavior of the present guide channel membrane.

Curved Guide Channels

Figure 8:
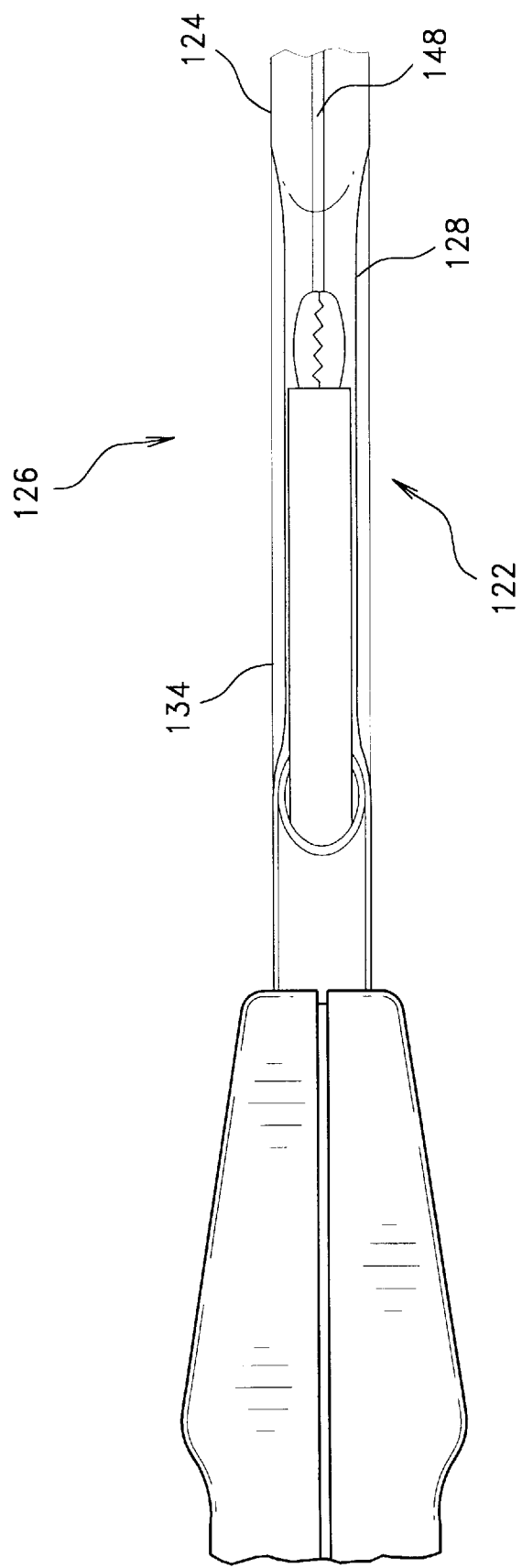
FIG. 8 is a close-up, broken-away view of the access device of FIG. 6 illustrating a guide platform or guide rail formed in conjunction with guide channel which guides and supports the secondary instrument along the curved guide channel.

FIGS. 7 and 8 illustrate another advantage of the present guide channel 118 relating to its ability to actually guide a rigid or semi-rigid instrument being deployed through it along a curved path. This advantage can best be described in light of the following background information. As shown in FIG. 1, a distal end 146 of the introducer 100 of the present invention is curved slightly. This curvature provides certain advantages, depending upon the endoscopic surgical procedure being performed. In this case, the introducer 100 of FIG. 1 can be used in performing a hysteroscopy, wherein an angle of curvature θ in the range of 5°–15° in the introducer 100 is advantageous in navigating the uterine canal. This curvature, as noted above, can also be used to gently move tissue out of the way in order to achieve advancement of the endoscope/introducer combination 110/100 to the desired location. With recent advancements in endoscopes, curvatures in these ranges, and even up to 30°, can be achieved without damage to the optical systems of the endoscopes.

However, another advantage of a curved introducer is illustrated in FIG. 7. As shown therein, an endoscope 110 which provides vision out of the curved distal end 146 of an introducer is able to sweep out a larger field of vision upon rotation of said introducer 100. This is illustrated in FIG. 7 by a first and second position (in phantom) of the distal end 146, rotated 180 degrees apart. This is a particular advantage in the case of rigid or semi-rigid endoscopes which do not have articulation means mounted at the distal end. In order to achieve this degree of curvature, as noted above in connection with FIGS. 3 and 4, the endoscopic tube 132 can be constructed from a strong and rigid stainless steel material which can be preformed or bent to the desired curvature. While this material will provide the rigidity, strength, and protection for the endoscope 110, it does not in and of itself solve the problems of secondary channels formed in such curved surgical access devices. Thus, secondary channels of the prior art were constructed to be used only with straight instruments or flexible instruments, such as catheters.

The guide channel 118 of the present invention accommodates a rigid or semi-rigid instrument which experiences a curve along its shaft as it is inserted through the guide channel. Thus, the guide channel 118 of the present invention makes possible another category of endoscopic surgical procedures requiring a curved but rigid or semi-rigid instrument. First, as noted above, the guide channel membrane 140 is constructed from an extremely strong material in order to withstand the stresses on it caused by a biased instrument mounted therein. Nonetheless, it is important that the secondary instrument being advanced through the guide channel 118 is provided with a smooth and straight passage. Any slippage or lateral movement may cause damage to the guide channel 118 and/or discomfort to the patient.

Moreover, the guide channel 118 may be located at a number of different circumferential locations with respect to the main or endoscopic channel 122. Thus, as shown in FIG. 7 in phantom, the guide channel 118 is located at the bottom of the main channel curvature. This longitudinal location may be considered "inboard" with respect to the curvature of the introducer 100. However, the guide channel 118 may also be positioned, as needed or desirable for a particular procedure, "outboard" of the introducer curvature (e.g., on the upper portion of the introducer 100 as oriented in accordance with FIG. 7) or "sideboard" (e.g., on one or more lateral sides of the introducer 100). At any of these various locations, the curved instrument will exert, due to the bias or spring force it causes as it bends, to apply a force on the outer sheath 134 of the main channel 122 and/or the guide channel 118.

Figure 9:
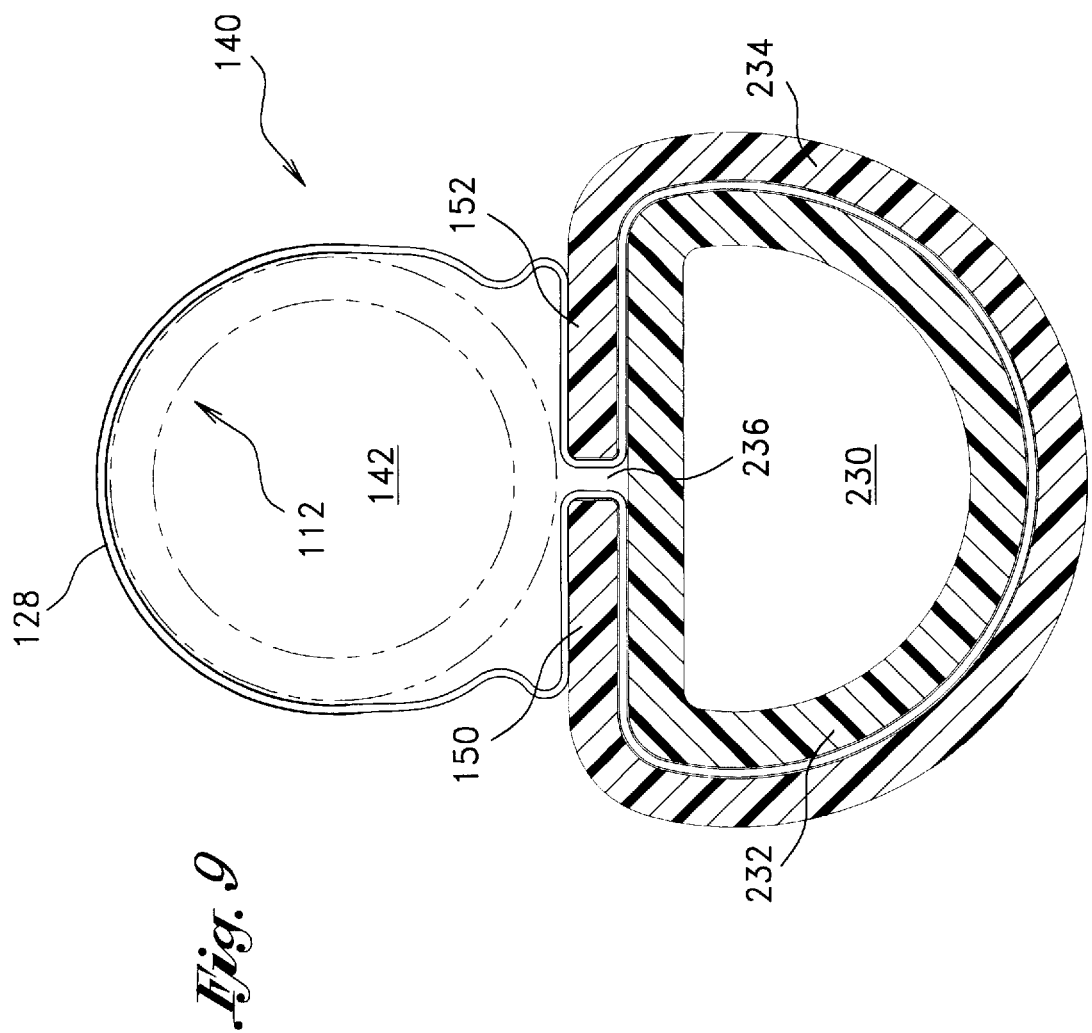
FIG. 9 is a cross-sectional view of another embodiment of the surgical access device of the present invention illustrating other guide channel and guide platform configurations, together with the manner in which the guide channel membrane is formed with respect thereto.

Thus, as illustrated in FIG. 8, the guide channel 118 of the present invention is provided with a guide platform or other type of guide rail 148 in order to actually guide the instrument 112 in its path along the guide channel 118. Thus, even though the instrument may be bending and flexing, it will tend to be retained in its path along the guide platform 148, which acts as a rail or track for the instrument to follow. As illustrated in FIG. 8, in one preferred embodiment the guide rail 148 comprises the slit 136 in the split sheath 134 of the main endoscopic channel 122. The longitudinal guiding capabilities of this slit 136 are also illustrated in FIG. 4. However, other guide platform configurations are possible, as illustrated in FIG. 9. FIG. 9 depicts a D-shaped main tube 232 which has a flattened area 150, 152 for instrument travel. This flattened area could also contain recesses or slots (not shown) to further facilitate directed insertion of the instrument. In any particular guide channel 118 and guide rail 148 configuration, the guide channel membrane 140 is able to assume a number of storage or set positions, as described above.

Thus, as illustrated in FIG. 9, the guide platform 148 may be flattened or may be provided with lateral walls 150, 152 in order to provide sure guidance for the curved instrument. These lateral walls may also have upward projections (not shown) so as to contain more securely the sides of the instrument 112. Therefore, in accordance with an important advantage of the present invention, the surgical access device can be used to guide an instrument along a specified path with respect to the main channel 122 so that it achieves accurate placement with respect to a specific location at the distal end of the access device 100.

Distal Portion

Figure 10:
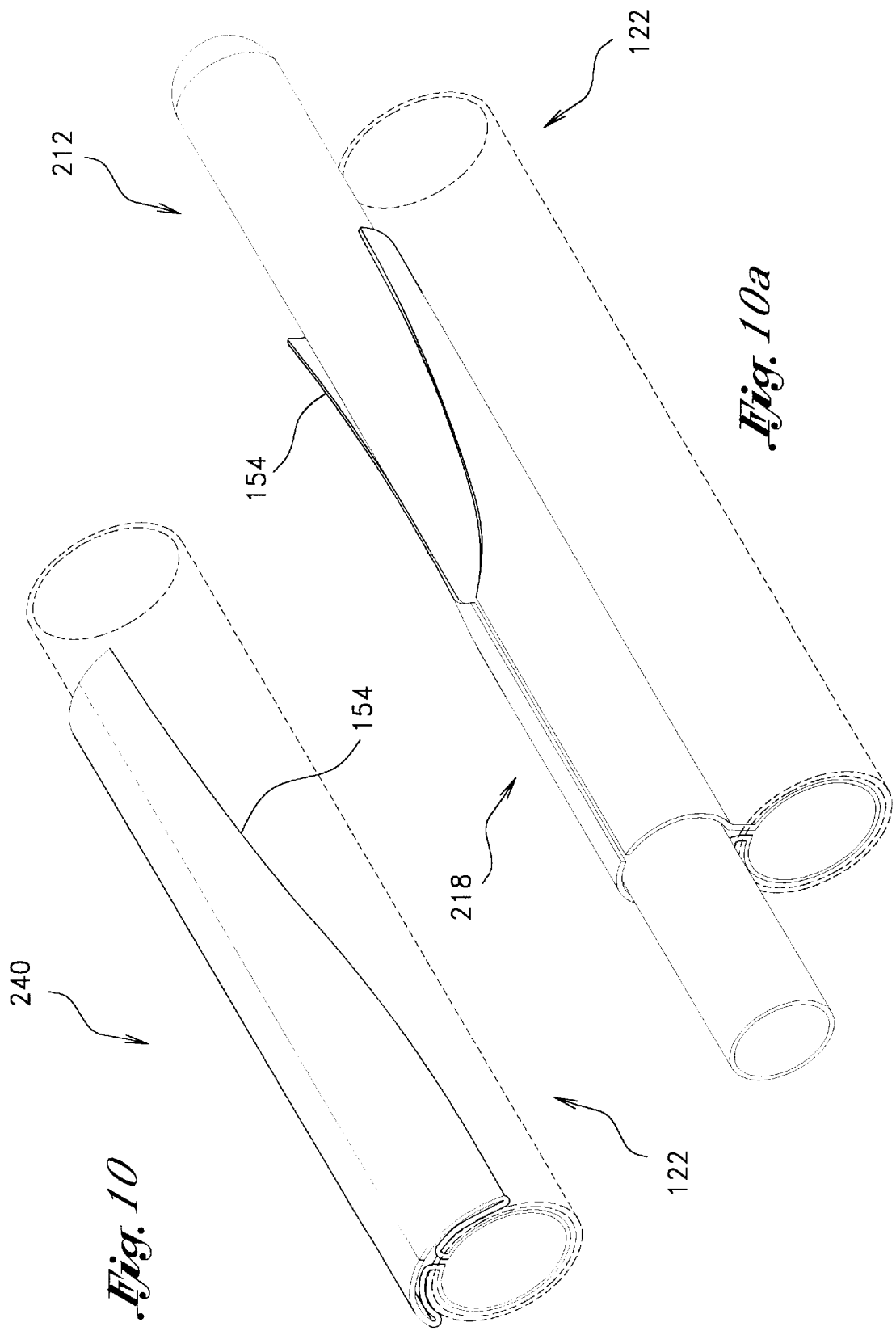
FIG. 10 is another embodiment of the guide channel of the present invention illustrating a guide channel membrane which is perforated or otherwise slit in order to exhibit unique or specialized release characteristics.

FIGS. 10 and 10a illustrate an alternate embodiment of a guide channel 218 of the present invention, which is characterized by a perforated or serrated guide channel membrane 240. As noted in FIGS. 10 and 10a, the guide channel membrane 240 is provided with a reduced diameter in the region of its distal tip 154. However, in this region or at other regions along the longitudinal length of the guide channel 218, the membrane 240 is perforated or serrated in order to facilitate its release as a secondary instrument 212 is advanced. Furthermore, the perforations or slits can be such that the guide channel 218 opens up completely in order to allow instrument access to the lateral regions of the access device. Such perforated or serrated guide channels 218 also provide other guide channel storage options, as well as other advantages which will be apparent to one of ordinary skill.

Figure 11:
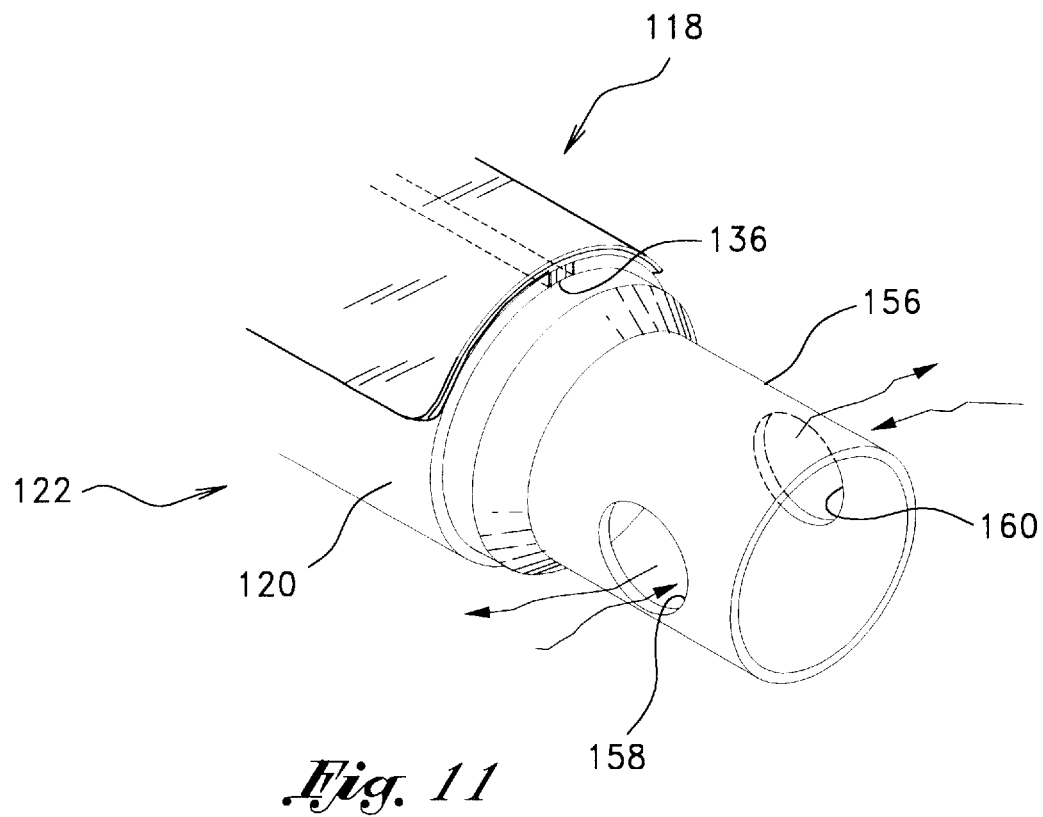
FIG. 11 is a close-up perspective view of the distal tip of the present access device illustrating the manner in which the guide channel may be sealed to prevent contamination or damage to the guide channel upon introduction of the access device into the body.
Figure 11A:
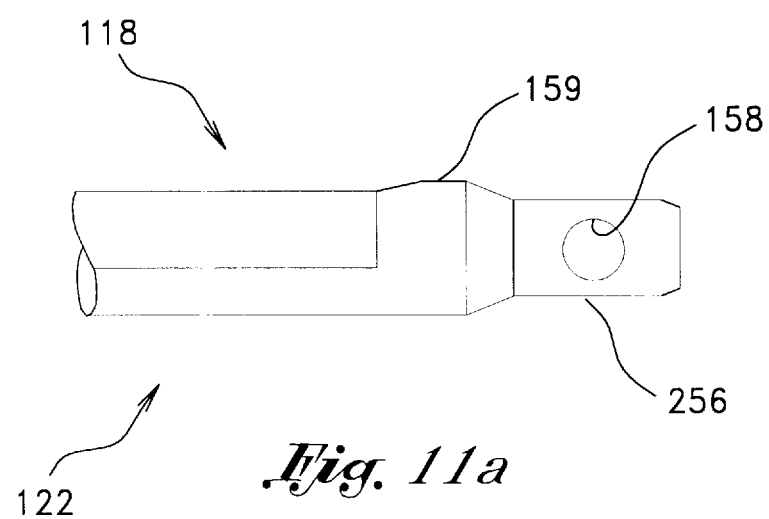
FIG. 11a is a close-up perspective view of an alternative embodiment of the distal tip of the present access device illustrating another manner in which the guide channel may be sealed to prevent contamination or damage to the guide channel upon introduction of the access device into the body.

FIG. 11 illustrates one embodiment of a distal tip 156 of the present introducer 100. In this embodiment, a tapered distal profile of the access device 100 facilitates the insertion process; however, the extreme distal edge is rounded or blunt in order to avoid damage to the tissue. Holes 158, 160 shown in the distal tip 156 are necessary to provide aspiration and avoid choking of irrigation media. In this embodiment, the guide channel at the distal tip 156, which is shown folded back on the outer surface 120 of the split sheath 134, can be securely sealed to the body of the introducer 100 by a heat seal process. Thus, the guide channel 118 is sealed and is impervious against contamination or distortion as the access device 100 is introduced into the body. An alternative embodiment of the distal tip 256 is shown in FIG. 11a. The distal end of the introducer can be shaped so as to have an annular mound 159 at the distal tip of the guide channel 118 and just proximal of the distal tip of the access device 100. Likewise, this mound 159 can serve to protect the distal end of the guide channel 118 against contamination or damage as the access device 100 is introduced into the body and navigated through its various anatomy.

Proximal Housing Portion

As explained above in connection with FIG. 1, the proximal housing portion 104 of the present invention surrounds the main endoscopic channel 122 and a merge channel 162 positioned above it in FIG. 12. The merge channel 162 allows an endoscope 110 or secondary instrument 112 to be inserted through it for deployment through the guide channel 118, shown in its predeployment position in FIG. 12. The merge channel 162 also allows a proximal handle 113 of the instrument 112 to be offset or displaced with respect to any endoscope or instrument inserted in the main channel 122 in order to facilitate use of the access device 100 by the surgeon.

Figure 13:
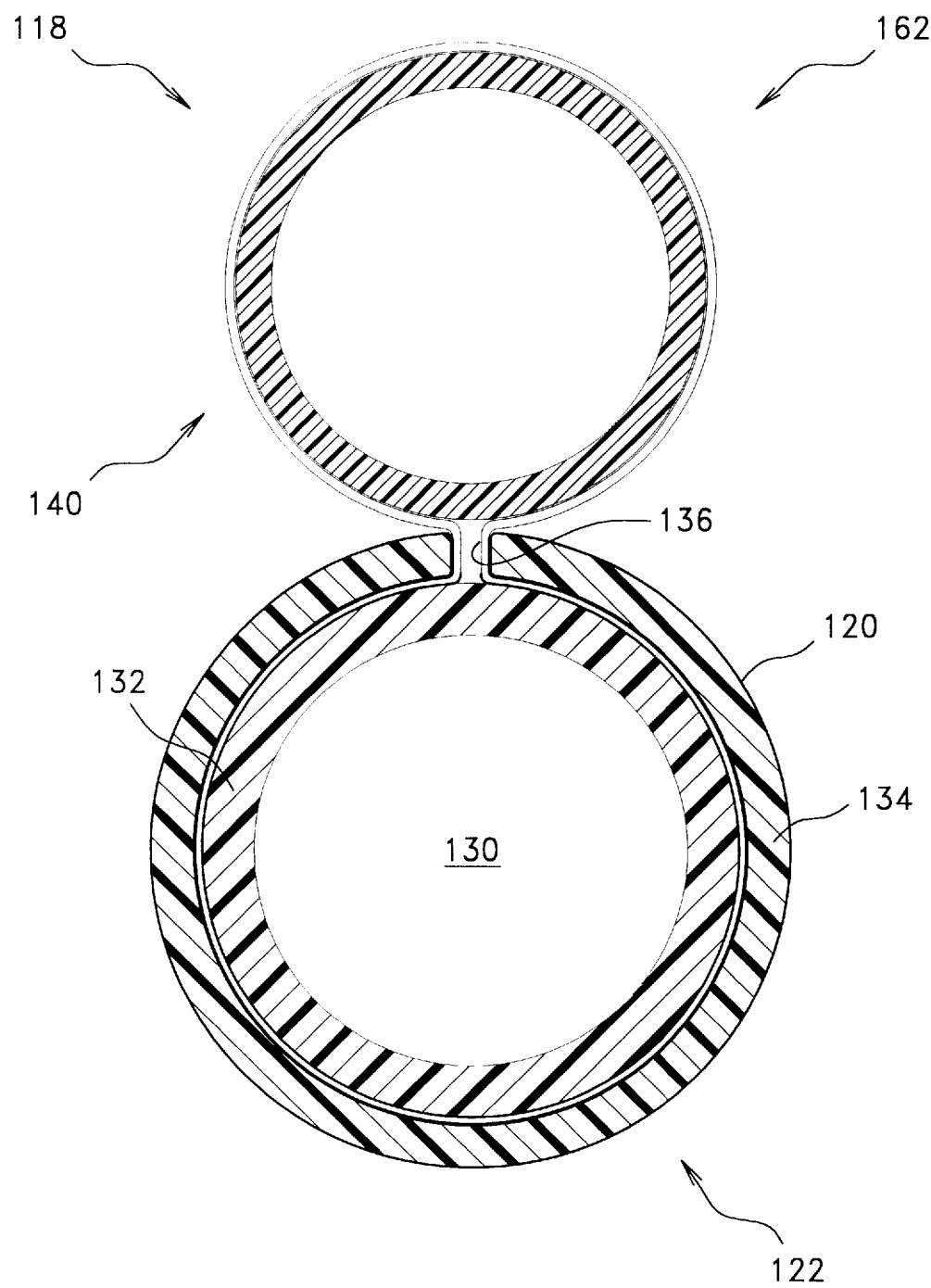
FIG. 13 is a cross-sectional view taken along lines 13—13 of FIG. 12 illustrating the merge channel and main channel distal the proximal housing of the present access device.

With reference to FIGS. 12 and 13, the proximal housing portion 104 of the surgical access device 100 of the present invention can be described. FIG. 12 is a partial cross-sectional view of the side of the access device 104, while FIG. 13 is a cross-sectional view taken along lines 13—13 of FIG. 13 in which is illustrated the piggyback arrangement of the main or endoscopic channel 122 and the merge channel 162 of the housing 104.

With reference to FIG. 12, it will be seen that the merge channel 162 converges upon the main channel 122 at a shallow angle φ, gradually becoming asymptotic or tangential thereto. The merge angle φ should be sufficient to allow a slight bending or curvature in the instrument being inserted through the merge channel 162 and into the guide channel 118; preferably, an angle φ of about 4°–30° is satisfactory with 11° preferable.

At the extreme proximal end of the housing portion 104, there is shown an inflow conduit 106 associated with the main channel 122 and an outflow conduit 108 associated with the merge channel 162. Depending upon the procedure being performed, the inflow conduit 106 may be utilized to pass distention or irrigation media down the main channel 122 to the distal end of the access device 100. Having the distension media run through the main tube 132 and around the endoscope 110 also allows for fluid to travel across the optics at the distal end of the endoscope 110 keeping this area free of blood and debris thereby improving visualization. The outflow channel 108 can be used to provide aspiration or other evacuation of fluids. Also, of course, the function of these conduits 106, 108 can be reversed or utilized in connection with multiple channels, as the case necessitates. In each case, duckbill valves 166, 168 are formed at the main or endoscopic port 14 and at the instrument port 116 in order to prevent the escape of fluids prior to insertion of the instruments into these respective channels. Likewise, O-ring structures or washer elements prevent the escape of fluids around an endoscope or instrument when inserted through the ports 114, 116. However, it will be understood that other types of valving and conduit mechanisms can be utilized in connection with the present access device.

The cross-sectional view of FIG. 13 also illustrates the association of the guide channel membrane 140 with respect to the merge channel 162. That is, the membrane 140 is shown extending through the slit or neck 136 in the split sheath 134 and completely around the merge channel 162. Advantageously, the guide channel membrane material can be heat formed onto both channels in order to provide some rigidity and strength to the proximal housing portion 104 of the access device 100. In fact, the membrane 140 can be extended proximally any desired distance, as shown in FIG. 12.

Method of Construction

Figure 14:
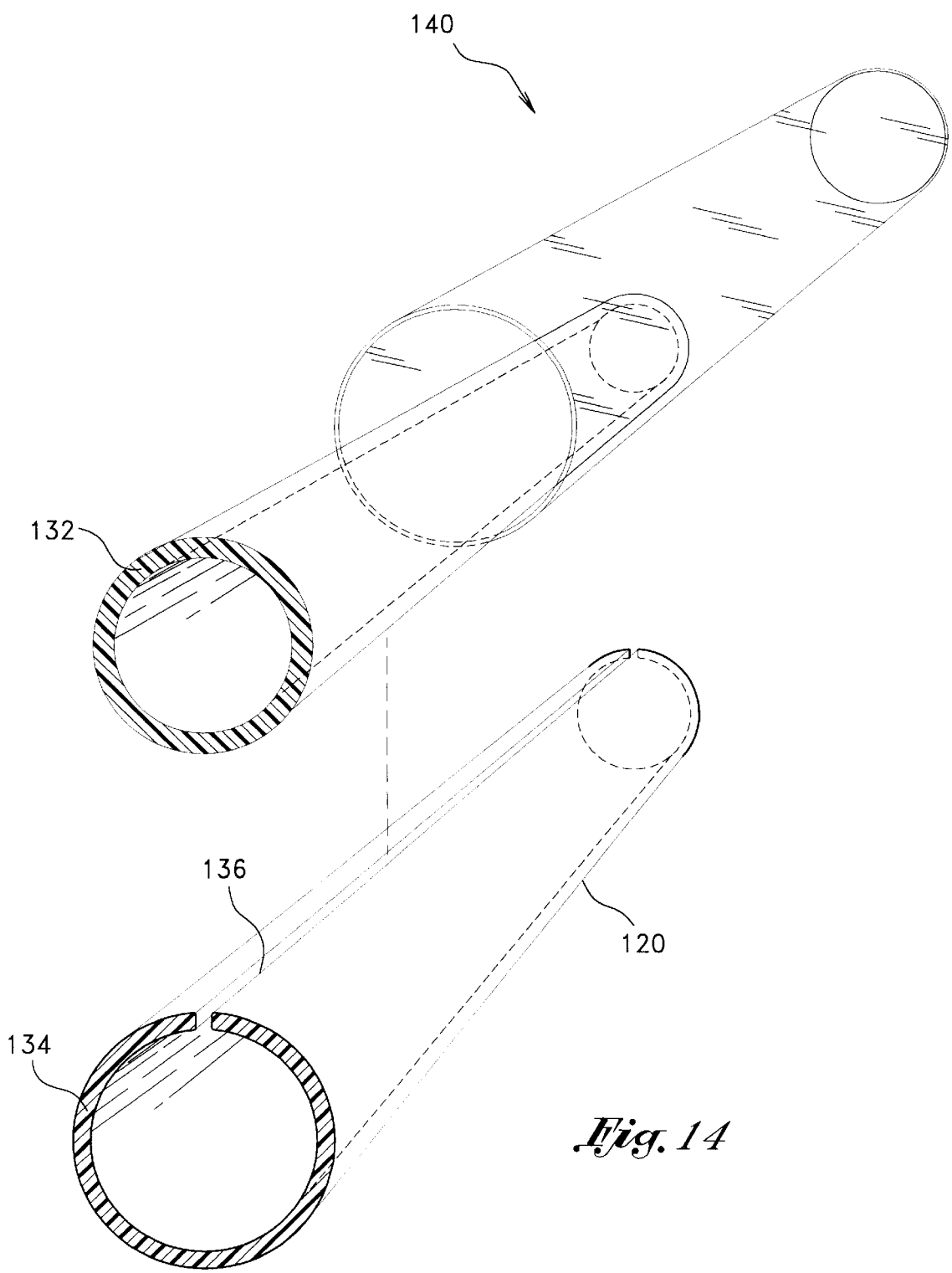
FIG. 14 is an exploded view of the present access device illustrating the method of its construction.

FIG. 14 is an exploded view of the present access device, illustrating a method of construction of the guide channel 118. Preferably, the main tubing 132 is preformed into the desired configuration, including any curvature. The guide channel membrane 140, which may take the form of an extruded tubing, as illustrated in FIG. 14, or other configuration, is then placed eccentrically around the main tubing 132. The nylon split sheath 134 is then mechanically expanded so as to surround the main tubing/membrane material, thereby capturing the membrane 140 around the tubing 132. During this process the excess membrane material is allowed to protrude through the slit or neck 136 in the split sheath 134 and is then folded or stored with respect to the access device 100 in accordance with various configurations discussed above. Covers or forms are placed onto the folded membranes and closely conform to the profile of the introducer 100. These elements keep the membrane 140 in close configuration prior to heat setting. Another method of forming a closely fitting mold is to swell an elastomeric tubing, such as silicone, with Freon. Prior to swelling, the silicone tubing is of a smaller diameter than the introducer 100. Once swollen and enlarged, the silicone tubing is slid over the folded membrane and introducer. When the Freon evaporates, the silicone tubing will resume its pre-enlarged state thereby creating a tightly fitting mold over the membrane. After heat setting, the silicone tubing can be removed from the introducer leaving the membrane in a tight configuration with the introducer. In any case, a moderate amount of heat is applied to the access device in order to thermoplastically set the guide channel membrane in its stored position. In one preferred embodiment, the PET material which comprises the guide channel membrane has a glass transition temperature of 180° F. Thus, the setting temperature used in this method of construction is preferably about 160° F. It will be noted in this regard that sterilization of the system is achieved at about 140° F.

The present method is not limited to that illustrated in FIG. 14 or described above. A number of other methods of construction will become apparent to those of ordinary skill. For example, because of the thermoplastic nature of the membrane material, heat forming, heat staking, or heat shrinking can easily be employed in other aspects of the construction method. Although most costly, adhesives or other mechanical fasteners can be utilized. Some adhesive systems can be effectively incorporated into the design of the membrane material, main tube or slit sheath by making these tubes as a co-extrusion with a secondary bonding material as a composite within the tubing material or body in which thermal bonding techniques can be employed. Heat-activated or hot-melt adhesives, UV cured adhesives, or pressure-sensitive adhesive systems can also be used to facilitate attachment of the membrane channel, such as the embodiment of FIGS. 3b and 3c, wherein the membrane is mounted directly on the hypotube. Such techniques can also be used for keeping the folded membrane tacked down onto the surface of the main tube.

Method of Use

In accordance with the operation of the present invention, a method of use comprises the steps of inserting a surgical access device into an opening in the patient's body (this step simultaneously comprising the insertion of an endoscope or other visualization device or other instrument into the body through said surgical access device or sequentially inserting the visualization device through the surgical access device and into the body after the surgical device is already in position), storing in connection with the body of the surgical access device one or more secondary guide channels and setting said guide channel in its storage position so as to provide a surgical access device including the guide channel with the profile which is substantially equivalent to the profile of the surgical access device without the guide channel, which may include visualizing by means of the endoscope the internal anatomy or tissue of the patient, and releasing the guide channel from its storage position with respect to the surgical access device so as to permit insertion into the patient's body of a secondary surgical instrument (or an endoscope or other visualization device), said releasing step being performed simultaneously with the insertion of said secondary instrument. The method may also comprise the steps of providing in connection with the guide channel a platform, rail, or track and guiding said secondary instrument through the guide channel along said platform, rail, or track. Clearly, because of the versatility of the surgical access device of the present invention, a number of methods of use are available.

In conclusion, the surgical access device of the present invention, including the guide channel and method for constructing same, represents a marked advancement in the art of secondary, expandable endoscopic surgical channels. Thus, it should be understood that the scope of the present invention is not to be limited by the illustrations or foregoing description thereof, but rather by the appended claims, and certain variations and modifications of this invention will suggest themselves to one of ordinary skill in the art.

What is claimed is:

1. A surgical access device for providing at least one auxiliary lumen for the insertion into a patient's body of an instrument, endoscope, or other visualization device, said surgical access device having an outer surface defining at any particular location along its longitudinal axis, a cross-sectional profile, said device comprising:

a first channel providing a first lumen for the insertion of an instrument, endoscope or other visualization device; and at least one secondary channel providing an auxiliary lumen for the insertion of an instrument, endoscope, or other visualization device, said secondary channel being mounted on said surgical access device so as to be positioned along said outer surface thereof, said secondary channel being constructed from a substantially noncompliant membrane having a pre-dilated position and a dilated position, which, in the pre-dilated position, is set in a self-retaining position which closely conforms to said outer surface.

2. The access device of claim 1, wherein said auxiliary lumen is self-adjusting to dilate only so far as necessary to admit the passage of an instrument being advanced through the auxiliary lumen.

3. The access device of claim 1, wherein the secondary channel is adapted to receive instruments having various cross-sectional profiles and to hold said instrument inserted therethrough securely within said auxiliary lumen.

4. A surgical access device for providing at least one auxiliary lumen for the insertion into a patient's body of an instrument, endoscope, or other visualization device, said surgical access device having an outer surface defining at any particular location along its longitudinal axis a cross-sectional profile, said device comprising:

a first channel having a first lumen with an open distal end for the insertion of an instrument, endoscope or other visualization device; and at least one secondary channel adapted to be dilated, said secondary channel providing an auxiliary lumen for the insertion of an instrument, endoscope, or other visualization device, said secondary channel constructed from a membrane which is self-conformable to the outer surface of said device such that, prior to dilation of said secondary channel, said membrane is folded to minimize the profile of said surgical access device.

5. A surgical access device for providing at least one auxiliary lumen for the insertion into a patient's body of an instrument, endoscope, or other visualization device, said surgical access device having an outer surface defining at any particular location along its longitudinal axis, a cross-sectional profile, said device comprising:

a first channel having an open distal end and providing a first lumen for the insertion of an instrument, endoscope or other visualization device; and at least one secondary channel adapted to be expanded from a first pre-dilated position to a second dilated position providing an auxiliary lumen for the insertion of an instrument, endoscope, or other visualization device, said secondary channel being constructed from a substantially noncompliant membrane which, prior to dilation of said secondary channel, is self-retained in said pre-dilated position along the outer surface of the device, such that said membrane closely conforms to said outer surface.

6. The access device of claim 5, wherein said secondary channel is easily collapsible from said second dilated position to said first pre-dilated position.

7. The access device of claim 5, wherein said membrane is thermoplastically settable.

8. The access device of claim 5, wherein said membrane is thermally, mechanically and/or chemically settable.

9. The access device of claim 8, wherein said membrane comprises polyethylene terephthalate.

10. A surgical access device, comprising:
a first channel; and
at least one secondary channel providing an auxiliary lumen for the insertion of an instrument, endoscope, or other visualization device, said secondary channel being constructed from a substantially inelastic membrane having a first storage position in which said membrane is initially self-retained and a second released position in which said membrane is dilated so as to allow passage of said instrument, endoscope, or other visualization device.

11. A channel adapted to be used with a percutaneous surgical access device so as to provide an auxiliary lumen for the insertion of an instrument, endoscope, or other visualization device, said channel comprising:
a substantially noncompliant membrane which is thermally, mechanically, and/or chemically settable so as to be self-retained in a first folded pre-expanded position and capable of being unfolded to form a wide variety of channel configurations.

12. The channel of claim 11, wherein said membrane is folded in said pre-expanded position and coupled to the access device so as to only negligibly increase the size of the access device.

13. A method of providing access to an internal site in a patient, comprising the steps of:
providing an access device having a proximal end, a distal end and an elongate body extending therebetween,
said device comprising a first lumen having a substantially fixed interior cross-sectional area and an open distal end and at least one second lumen defined at least in part by a substantially inelastic flexible wall, said second lumen having an internal cross-sectional area that is movable from a first, reduced area to a second, enlarged area said wall initially self-retained so that the internal cross-sectional area is said first, reduced area;
advancing the access device into the patient while the second lumen is in the first, reduced cross sectional area configuration; and
enlarging the cross-sectional area of the second lumen from the first, reduced cross-sectional area to the second enlarged cross-sectional area to provide access to an internal site in the patient by way of said second lumen.

14. A method of manufacturing a multilumen access device having a cross-sectional profile, comprising the steps of:
providing an elongate tubular element having a tubular wall with a radially outwardly facing surface thereon and an open distal end;
providing a substantially noncompliant, flexible tubular sleeve having a central lumen extending axially therethrough, said sleeve also having a radially inwardly facing surface thereon, said inwardly facing surface being larger than said outwardly facing surface of said tubular element;
positioning the tubular element eccentrically within the tubular sleeve;
securing the inwardly facing surface of the tubular sleeve to the outwardly facing surface of the tubular element circumferentially around the tubular element through an angle of at least about 180°; and
folding the excess tubular sleeve to closely conform to the outer surface of the tubular element.

15. A method as in claim 14, wherein said securing step comprises the steps of providing an elongate flexible tubular sheath having an axially extending lumen therethrough, and an axially extending slit in the wall thereof, and positioning said sheath eccentrically about the tubular sleeve.

16. A method as in claim 5, wherein the diameter of the tubular sleeve when the sleeve is in a cylindrical configuration is within the range of from about 25% to about 500% larger than the outside diameter of the tubular element.

17. A method as in claim 14, wherein said securing step is accomplished using adhesives.

18. A method as in claim 14, wherein said securing step is accomplished by heat bonding.

19. A method of expanding the effective diameter of an access site, comprising the steps of:
providing an elongate rigid walled introducer having an elongate tubular body with at least a first lumen extending axially therethrough and defined within a substantially rigid wall, the wall defining the first lumen having a radially inwardly facing surface and a radially outwardly facing surface, the introducer also having at least a second lumen extending axially through the body, said second lumen comprising a substantially inelastic collapsible wall;
percutaneously introducing the introducer into the patient while the wall of the second lumen is self-retained in a collapsed configuration; and
expanding the second lumen, wherein said expanding step enlarges the effective diameter of said access site.

20. A method as in claim 19 further comprising the step of presetting the wall of the second lumen in the collapsed configuration to complement a portion of the outwardly facing surface of the wall defining the first lumen.

21. The access device of claim 19, wherein the outer surface of said wall of the second lumen is lubricous to facilitate the step of introducing the introducer into the patient.

22. A surgical access device having proximal and distal ends, comprising:
a first channel having a first lumen extending axially through the device and a distal opening at the distal end of the device;
a second channel having a second lumen extending axially through the device, said second channel defined at least in part by a substantially inelastic flexible wall, said second channel initially self-retained in a first, reduced configuration with said second lumen having an internal cross-sectional area of a first reduced area,
said second channel being adapted to expand from said first configuration to a second, enlarged configuration in which said second lumen has an internal cross-sectional area of a second, enlarged cross-sectional area;
wherein both of the first and second channels extend substantially all the way to the distal end of the device.

23. The access device of claim 22, wherein said wall is folded and thermoplastically set in said first, reduced configuration.

24. A surgical access device for providing at least one auxiliary lumen for the insertion of an instrument, endoscope, or other visualization device into a patient's body, said surgical access device having an outer surface defining a cross-sectional profile at any particular location along its longitudinal axis, said device comprising:

an elongate tubular body containing a first lumen for the insertion of an instrument, endoscope or other visualization device, said first lumen having a distal end; and at least one secondary lumen for the insertion of an instrument, endoscope, or other visualization device, said secondary lumen positioned along an outer surface of the tubular body, said secondary lumen defined within a flexible tubular membrane which extends substantially all the way to the distal end and which is moveable from a first position in which the membrane is folded and the access device has a low, introduction profile, and a second position in which the membrane is unfolded and the access device has a relatively larger profile.

25. A surgical access device as in claim 24, wherein the membrane is preset in the folded position.

26. A surgical access device as in claim 24, wherein the membrane comprises a substantially inelastic material.

27. A surgical access device as in claim 26, wherein the membrane comprises polyethylene terephthalate.

28. A surgical access device as in claim 26, wherein the tubular body comprises stainless steel.

29. The access device of claim 1, wherein said membrane is made from an inelastic polymer.

* * * * *